US008585604B2

(12) United States Patent
Bennett et al.

(10) Patent No.: US 8,585,604 B2
(45) Date of Patent: Nov. 19, 2013

(54) INTEGRATED PATIENT CARE

(75) Inventors: Tommy D. Bennett, Shoreview, MN (US); Yong Kyun Cho, Maple Grove, MN (US); Randolph M. Biallas, Littleton, CO (US)

(73) Assignee: Medtronic, Inc., Minneapolis, MN (US)

( * ) Notice: Subject to any disclaimer, the term of this patent is extended or adjusted under 35 U.S.C. 154(b) by 273 days.

(21) Appl. No.: 12/915,992

(22) Filed: Oct. 29, 2010

(65) Prior Publication Data
US 2012/0108984 A1 May 3, 2012

(51) Int. Cl.
*A61B 5/02* (2006.01)
(52) U.S. Cl.
USPC .......................................................... 600/485
(58) Field of Classification Search
USPC ............................. 600/300, 301, 485; 705/2
See application file for complete search history.

(56) References Cited

U.S. PATENT DOCUMENTS

| | | |
|---|---|---|
| 6,280,409 B1 | 8/2001 | Stone et al. |
| 6,398,727 B1 | 6/2002 | Bui et al. |
| 6,599,250 B2 | 7/2003 | Webb et al. |
| 7,065,409 B2 | 6/2006 | Mazar |
| 7,590,449 B2 | 9/2009 | Mann et al. |
| 7,717,854 B2 | 5/2010 | Mann et al. |
| 7,751,901 B2 | 7/2010 | Mazar et al. |
| 7,757,690 B2 | 7/2010 | Stahmann et al. |
| 7,801,604 B2 | 9/2010 | Brockway et al. |
| 2002/0103442 A1 | 8/2002 | Mulligan et al. |
| 2003/0036683 A1 | 2/2003 | Kehr et al. |
| 2004/0122487 A1 | 6/2004 | Hatlestad et al. |
| 2004/0147969 A1 | 7/2004 | Mann et al. |
| 2004/0181262 A1 | 9/2004 | Bauhahn |
| 2004/0215049 A1 | 10/2004 | Zdeblick et al. |
| 2005/0065567 A1 | 3/2005 | Lee et al. |
| 2005/0085734 A1 | 4/2005 | Tehrani |
| 2005/0187789 A1 | 8/2005 | Hatlestad et al. |
| 2005/0216067 A1 | 9/2005 | Min et al. |

(Continued)

FOREIGN PATENT DOCUMENTS

| | | |
|---|---|---|
| WO | 2009/055207 A2 | 4/2009 |
| WO | 2010/051185 A1 | 5/2010 |

OTHER PUBLICATIONS

International Search Report and Written Opinion from corresponding PCT Application Serial No. PCT/US2011/034348 dated Oct. 5, 2011 (8 pages).

(Continued)

*Primary Examiner* — Navin Natnithithadha
*Assistant Examiner* — Etsub Berhanu
(74) *Attorney, Agent, or Firm* — Michael C. Soldner

(57) ABSTRACT

A therapy regimen, e.g., a contingent medication prescription, may be created and automatically distributed to a patient via an integrated patient care system. A clinician may create therapy instructions by at least associating patient conditions with one or more therapy regimens, e.g., medication prescriptions. In some examples, the integrated patient care system may present historical condition data to the clinician to aid the clinician with creating and/or updating the therapy instructions specific to the patient. A therapy module of the integrated patient care system may use the therapy instructions to automatically select a therapy regimen from the therapy instructions based on a patient condition detected based on a sensed physiological parameter. The physiological parameter of the patient may be sensed by an implanted or external sensor. In some examples, the therapy regimen can be presented to the patient according to a predetermined schedule or in response to the detected condition.

21 Claims, 21 Drawing Sheets

(56) References Cited

U.S. PATENT DOCUMENTS

| | | |
|---|---|---|
| 2006/0167514 A1 | 7/2006 | Kjellstrom et al. |
| 2006/0167516 A1 | 7/2006 | Kjellstrom et al. |
| 2006/0224190 A1 | 10/2006 | Gill et al. |
| 2007/0065363 A1 | 3/2007 | Dalal et al. |
| 2007/0161914 A1 | 7/2007 | Zdeblick et al. |
| 2007/0271117 A1 | 11/2007 | Klein et al. |
| 2008/0097175 A1* | 4/2008 | Boyce et al. ............. 600/323 |
| 2009/0036757 A1 | 2/2009 | Brockway et al. |
| 2009/0043289 A1 | 2/2009 | Zhang et al. |
| 2009/0076338 A1 | 3/2009 | Zdeblick et al. |
| 2009/0076350 A1 | 3/2009 | Bly et al. |
| 2009/0076401 A1 | 3/2009 | Mazar et al. |
| 2009/0275848 A1 | 11/2009 | Brockway et al. |
| 2009/0299198 A1 | 12/2009 | Carney et al. |
| 2009/0312668 A1* | 12/2009 | Leuthardt et al. ............. 600/558 |
| 2010/0018530 A1 | 1/2010 | Schindhelm et al. |
| 2010/0113888 A1 | 5/2010 | Cho et al. |
| 2010/0113945 A1 | 5/2010 | Ryan |
| 2010/0228314 A1 | 9/2010 | Goetz |

OTHER PUBLICATIONS

International Preliminary Report on Patentability from international application No. PCT/US2011/034348, dated May 10, 2013, 7 pp.

* cited by examiner

| PRESSURE STATUS 112 | MEDICATION 114 | DOSAGE 116 | QUANTITY 118 | TIMES PER DAY 120 | ALTERNATE NAME 122 |
|---|---|---|---|---|---|
| VERY HIGH<br>> 31 mmHg | DRUG A | 60 mg | 3 | 1 | BLUE PILL |
|  | DRUG B | 2 mg | 1 | 1 | RED PILL |
| HIGH<br>> 26 mmHg | DRUG A | 60 mg | 1 | 1 | BLUE PILL |
|  | - | - | 0 | 0 | - |
| NORMAL<br>> 23 mmHg | - | - | 0 | 0 | - |
|  | - | - | 0 | 0 | - |
| LOW<br>> 10 mmHg | DRUG C | 100 mg | 3 | 2 | WHITE PILL |
|  | - | - | 0 | 0 | - |
| VERY LOW<br>> 5 mmHg | DRUG C | 100 mg | 5 | 1 | WHITE PILL |
|  | - | - | 0 | 0 | - |

FIG. 7

PATIENT INSTRUCTION SET

| Jane Doe | Same as yesterday | Jan 31, 2010 |

Take 4 of the 20 mg Lasix pills
(Lasix is your water pill, also called furosemide)

Transmitted today, check instructions again tomorrow

PATIENT INSTRUCTION SET

| Jane Doe | NEW PRESCRIPTION | Jan 31, 2010 |

Take 2 of the 20 mg Lasix pills
(Lasix is your water pill, also called furosemide)

Transmitted today, check instructions again tomorrow

PATIENT INSTRUCTION SET

| Jane Doe | NEW PRESCRIPTION | Jan 31, 2010 |

Take 0 of the 20 mg Lasix pills
(Lasix is your water pill, also called furosemide)

CALL YOUR CLINIC (555-555-5555)

PATIENT INSTRUCTION SET

Jane Doe       NEW PRESCRIPTION       Jan 31, 2010

Take 6 of the 20 mg Lasix pills
(Lasix is your water pill, also called furosemide)

Transmitted today, check instructions again tomorrow

PATIENT INSTRUCTION SET

Jane Doe       NEW PRESCRIPTION       Jan 31, 2010

Take 8 of the 20 mg Lasix pills
(Lasix is your water pill, also called furosemide)

CALL YOUR CLINIC (555-555-5555)

| Pressure State | Instructions | | |
|---|---|---|---|
| Very High (31 mmHg) | Take 3 Drug A pills (60 mg) each morning | Delete | Edit |
| | Take 1 Drug B pills (2 mg) each evening | Delete | Edit |
| | Call the Clinic (555-555-5555) | | |
| High (26 mmHg) | Take 3 Drug A pills (60 mg) each morning | Delete | Edit |
| Normal (23 mmHg) | Take 2 Drug A pills (40 mg) each morning | Delete | Edit |
| Low (10 mmHg) | Take 1 Drug A pills (20 mg) each morning | Delete | Edit |
| Very Low (5 mmHg) | No medication | Delete | Edit |
| | Call the Clinic (555-555-5555) | | |

FIG. 20

INTEGRATED PATIENT CARE

TECHNICAL FIELD

The disclosure relates to monitoring and treating a patient's medical condition.

BACKGROUND

Some medical conditions may require frequent monitoring and adjustment of treatment regimens. For example, the severity of and/or symptoms associated with a particular medical condition may have a propensity to change over time. Clinicians or other healthcare professionals may frequently monitor the patient's condition and adjust one or more treatment regimens when needed to effectively manage the medical condition.

SUMMARY

In general, this disclosure is directed to an integrated patient care system and techniques performed by the integrated patient care system for monitoring and treating a medical condition of a patient. A therapy regimen, e.g., a contingent medication prescription, may be created and automatically distributed to a patient via the integrated patient care system. The system may allow a clinician to create therapy instructions that associate patient conditions with one or more therapy regimens, e.g., contingent medication prescriptions. The system may provide historical condition data to the clinician to facilitate the creation or updating of the therapy instructions. Once the therapy instructions are created, a therapy module, e.g., an external computing device, may automatically select a therapy regimen from a plurality of therapy regimens for delivery to the patient based on a patient condition detected based on a physiological parameter sensed by one or more sensors. The sensor may be an implanted or external sensor that senses at least one physiological parameter, e.g., pulmonary artery pressure or transthoracic impedance. After the therapy regimen is selected, the system may present the therapy regimen to the patient, e.g., according to a predetermined schedule, in response to the detected condition, or at the request of the patient.

In one example, the disclosure is directed to a system that includes a clinician module configured to receive input that defines one or more therapy instructions specific to a patient, a sensor configured to sense a physiological parameter indicative of one or more conditions of the patient, and a processor configured to automatically select a therapy regimen from a plurality of stored therapy regimens based on the one or more conditions indicated by the sensed physiological parameter and the one or more therapy instructions. The system also includes a patient display configured to present the selected therapy regimen to the patient.

In another example, the disclosure is directed to a method that includes receiving input from a clinician at a clinician module, wherein the input defines one or more therapy instructions specific to a patient, and sensing a physiological parameter indicative of one or more conditions of the patient with a sensor. The method also includes, with a processor, automatically selecting a therapy regimen from a plurality of stored therapy regimens based on the one or more conditions indicated by the sensed physiological parameter and the one or more therapy instructions, and presenting the selected therapy regimen to the patient via a patient display.

In another example, the disclosure is directed to a system that includes means for receiving input from a clinician that defines one or more therapy instructions specific to a patient, means for sensing a physiological parameter indicative of one or more conditions of the patient, and means for automatically selecting a therapy regimen from a plurality of stored therapy regimens based on the one or more conditions indicated by the sensed physiological parameter and the one or more therapy instructions. The system also includes means for presenting the selected therapy regimen to the patient.

In another aspect, the disclosure is directed to an article of manufacture comprising a computer-readable storage medium. The computer-readable storage medium comprises computer-readable instructions for execution by a processor. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. The computer-readable medium may be nontransitory.

The details of one or more examples are set forth in the accompanying drawings and the description below. Other features, objects, and advantages will be apparent from the description and drawings, and from the claims.

BRIEF DESCRIPTION OF DRAWINGS

FIG. 7 is a conceptual diagram illustrating an example screen that may receive therapy instructions specifying contingent prescriptions from a clinician.

FIGS. 14A-14E are conceptual diagrams illustrating example screens presenting various therapy regimens based on detected patient conditions.

FIG. 19 is an example display that illustrates feedback from a patient related to a distributed therapy regimen.

FIGS. 20-21 are conceptual diagrams illustrating example screens that may be displayed to receive therapy instructions specifying contingent prescriptions from a clinician.

DETAILED DESCRIPTION

Figure 1:
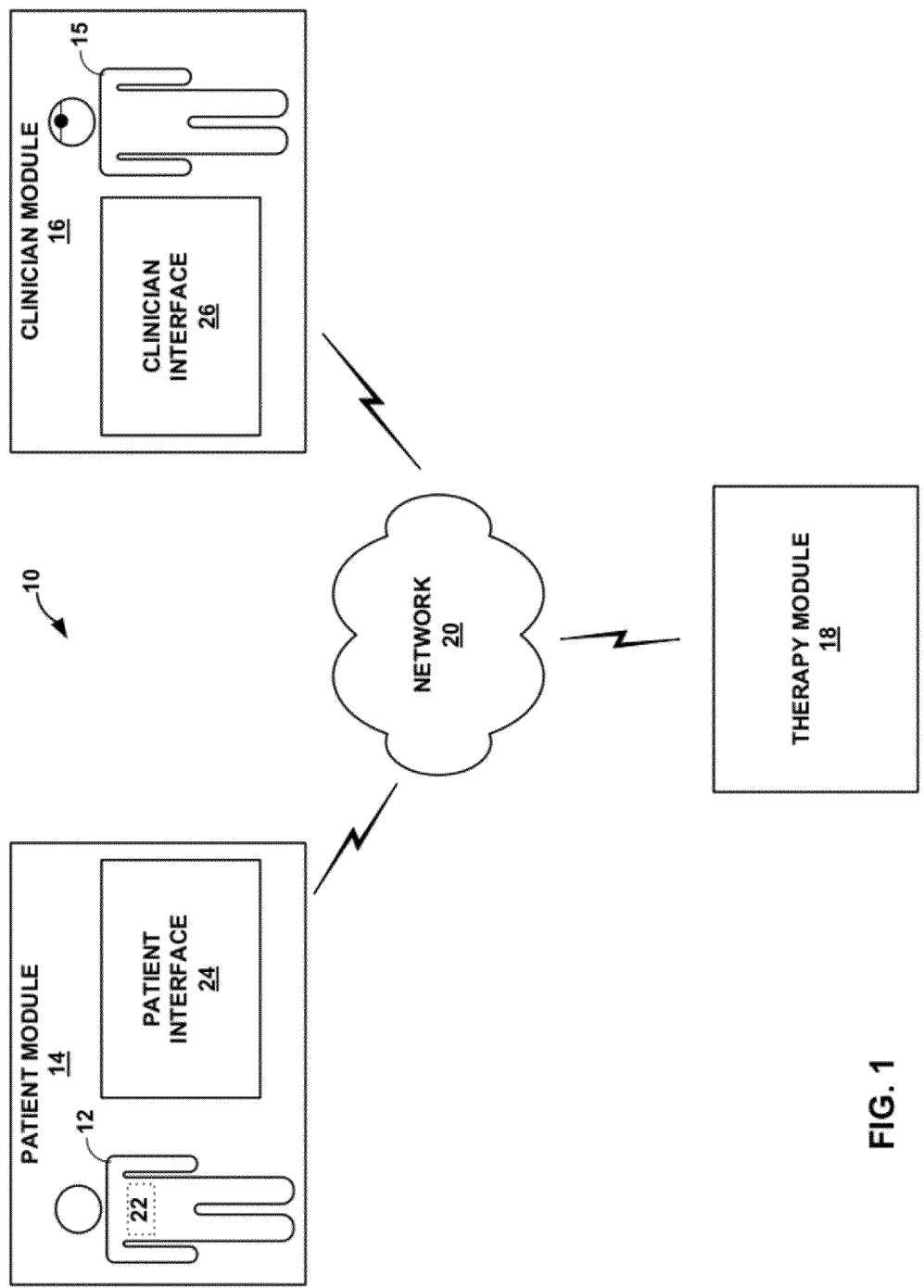
FIG. 1 is a conceptual diagram of an integrated patient care system for monitoring and treating a disorder of a patient.

Patients may suffer from medical disorders for which frequent monitoring and treatment modifications may be desirable. The degree or severity of the medical condition may have a propensity to change over time, or the patient may unpredictably exhibit new symptoms. Frequent monitoring and treatment modifications may help to more effectively reduce the severity of the medical condition and/or alleviate symptoms associated with the medical condition, or, in some examples, the frequent monitoring and treatment modifications may help to anticipate and prevent progression of the medical condition.

In one example, congestive heart failure (HF) may be such a medical condition requiring frequency monitoring and/or updates to therapy. Patients afflicted with HF may require daily monitoring to avoid transitioning into acute decompensated heart failure, or decompensation. Decompensation generally refers to exacerbated heart failure and can be characterized by certain signs and symptoms, e.g., shortness of breath and weakness, that may require urgent therapy or hospitalization. In some examples, decompensation may be induced by an intercurrent illness (e.g., pneumonia), myocardial infarction, one or more cardiac arrhythmias, uncontrolled hypertension, or failure of the patient to maintain a fluid restriction, diet, or medication regimen.

Although frequent monitoring by a clinician or other healthcare professional may be desirable, this demanding contact may be prohibitively inconvenient, time-consuming, and expensive for both the patient and the clinician. The systems and techniques described herein facilitate monitoring of one or more medical conditions in a manner that may be less expensive, less time-consuming, and more convenient for both the patient and the clinician compared to systems and techniques that require the patient to be physically present at the clinician's office or for the clinician to be physically present with the patient. For example, using the systems and techniques described herein, the clinician may set up therapy instructions that define associations, or relationships, between certain patient conditions and specific therapy regimens. In this manner, the clinician may set up contingent medication prescriptions that are individually prescribed only when called for by a detected patient condition. A sensor at the patient (e.g., implanted in the patient or external to and proximate the patient) senses a physiological parameter of the patient. An external computing device, e.g., a therapy module, may detect a condition of the patient based on an output from the sensor (e.g., the signal indicative of the physiological parameter).

Based on the detected condition, the external computing device automatically selects one of the therapy regimens and distributes or transmits the therapy regimen to the patient. In some examples, the patient may view the therapy regimen displayed on a patient display and take the appropriate action to modify treatment. For example, the patient may read the therapy regimen, and, in response, manually take the contingent medication prescription. In other examples, the system may include a delivery device (e.g., a pill dispenser) that automatically dispenses the prescribed medication to the patient according to the therapy regimen. In some examples, the patient may provide feedback regarding the therapy regimen, e.g., when the therapy was completed, a change in the condition, or any side effects, to the patient interface. This feedback may then be transmitted to the clinician for therapy review.

Although this disclosure generally describes an integrated monitoring system configured to monitor HF, the system may be configured to monitor other patient ailments, diseases or a combination of ailments, diseases and associated symptoms. In any case, the system may detect many patient conditions with one or more sensors and automatically select the appropriate therapy regimen.

FIG. 1 is a schematic illustration of integrated patient care system 10 for monitoring and treating a medical condition of patient 12. System 10 includes patient module 14, clinician module 16, therapy module 18, and network 20. Patient module 14, clinician module 16, and therapy module 18 are configured to communicate with one another via network 20. Although patient module 14, clinician module 16, and therapy module 18 may each be a different device or group of devices, one device may include two or more of the modules. For example, an external computing device with patient 12 may include patient module 14 and therapy module 18 and not require network 20 for communication with each other.

Patient module 14 includes any components necessary for integrating patient 12 into integrated patient care system 10. In the example illustrated in FIG. 1, patient module 14 includes sensor 22, which is configured to sense one or more physiological parameters of patient 12. Using the sensed physiological parameters, sensor 22 may sense one or more conditions of patient 12. Patient module 14 additionally includes patient interface 24 for interaction with patient 12, e.g., for presenting therapy regimens deliverable to patient 12, and/or receiving input from patient 12 (e.g., patient feedback). In addition, in the example illustrated in FIG. 1, patient 12 is schematically illustrated as part of patient module 14 to demonstrate that patient module 14 is associated with patient 12.

In some examples, patient module 14 may also include a processor for performing the techniques attributed to patient module 14 herein. In some examples, a processor may be included within a multi-function device or patient module 14. For example, patient module 14 may include a handheld computing device (e.g., programmer 72 illustrated in FIG. 2), a workstation computer, a personal digital assistant (PDA), a notebook computer, a tablet computer, or another personal computer or other electronic device, any of which may include the processor for performing the techniques attributed to patient module 14. In general, components described as processors of system 10 within this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

In some examples, patient module 14 may also include a memory for storing data. For example, in some examples, the memory may store data related to patient 12, e.g., health information of patient 12 or information identifying patient 12, physiological parameters sensed by sensor 22, detected conditions of patient 12, or any other information related to the medical condition of patient 12. The memory can include any suitable type of memory, such as random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Sensor 22 of patient module 14 may be any sensor configured to sense a physiological parameter of patient 12 useful for detecting a condition of patient 12 related to the patient's medical condition. In other words, the physiological parameter sensed by sensor 22 may be a specific value or signal generated from sensor 22, and a processor of patient module 14 may use this value or signal to detect conditions of the patient. As one example, sensor 22 may be a pressure sensor that senses a pressure value of patient 12, and a processor may detect a specific patient condition based on the pressure value, e.g., when the pressure value falls within a pressure range corresponding to the specific condition. Example types of sensor 22 may include a pressure sensor, a motion sensor (e.g., an accelerometer, gyroscope or pressure transducer), a temperature sensor (e.g., a thermometer), an acoustic sensor, or an impedance sensor. The type of sensor 22 may be selected based on the type of information required to detect and monitor the condition of patient 12. In one example, as described in further detail below with respect to FIGS. 2 and 3, sensor 22 may be a pressure sensor that is implanted within the right ventricle of the heart of patient 12 to sense pressure within the right ventricle indicative of patient 12 HF. In the examples described herein, sensor 22 is implanted within patient 12. However, in other examples, sensor 22 may be external to patient 12, e.g., an ultrasound sensor, one or more surface electrodes, or an activity sensor (also referred to as a motion sensor).

Patient interface 24 may be any user interface suitable for interaction with patient 12. For example, patient interface 24 may include a display and one or more input mechanisms (e.g., buttons or a touch screen display) that allow another component of system 10 to receive input from patient 12. The display may be a liquid crystal display (LCD), dot matrix display, organic light-emitting diode (OLED) display, touch screen, or any other device capable of delivering and/or accepting information. For visible indications of information, a display screen may suffice. For audible and/or tactile indications of information, patient interface 24 may further include one or more audio speakers, voice synthesizer chips, piezoelectric buzzers, or the like. Further, in some examples, patient interface 24 may include a printer configured to print out a distributed therapy regimen. Patient 12 may take the therapy regimen print-out away from patient module 14 as a reminder of the therapy regimen.

Input buttons for patient interface 24 may include a touch pad, increase and decrease buttons, emergency shut off button, and other buttons that may control a treatment delivered to patient 12. A processor of system 10 may control patient interface 24, retrieve data stored in a memory of system 10, store data within a memory of system 10, and/or transmit data from patient module 14 to another module of system 10.

In some examples, patient module 14 may include a delivery device that dispenses medication to patient 12 according to the therapy regimen received from therapy module 18. For example, the delivery device may be a pill dispenser in communication with the processor of patient module 14. Upon receiving the therapy regimen, the pill dispenser may dispense the appropriate medication type and dose at the specified time according to the therapy regimen. In this manner, a delivery device may be loaded with multiple medications that may eventually be prescribed by the therapy regimen. The delivery device may obviate the need for patient 12 to manually retrieve the appropriate medication from various bottles or select the appropriate dose. This can be useful, for example, if patient 12 has difficulty manually obtaining the correct medication in the correct dosage. In another example, the delivery device may be an intravenous drug delivery device. The therapy regimen may include control the rate at which drug is delivered to patient 12, such upon selecting a therapy regimen, patient module 14 may automatically adjust a rate at which a drug is delivered to patient 12 via the intravenous drug delivery device. The drug delivery device may not be intravenous in other examples.

Clinician module 16 may include any components necessary for integrating clinician 15 into integrated patient care system 10. In the example illustrated in FIG. 1, clinician module 16 includes clinician interface 26, which allows clinician 15 to communicate and exchange information with patient module 14 and therapy module 18 of system 10. Clinician 15 is schematically illustrated as part of clinician module 16 to demonstrate that clinician module 16 is associated with clinician 15. In some examples, clinician module 16 may also include a processor for performing the techniques attributed to clinician module 16 herein. In some examples, the processor may be included within a multi-function device of clinician module 16. For example, clinician module 16 may include a handheld computing device, a larger workstation computer, a PDA, a notebook computer, a tablet computer, or another multipurpose personal computer or dedicated computing device, any of which may include the processor for performing the techniques of clinician module 16. Although clinician interface 26 may be a user interface on a single device, clinician interface 26 may be accessible on a variety of devices as needed by clinician 15. For example, clinician 15 may be able to access clinician interface 26 via a clinician programmer, clinic workstation, tablet computer, webpage, or a consumer electronic device (e.g., a cellular telephone). In this manner, clinician module 16 may be provided by a clinic server or other remote computing device and clinician 15 may update therapy instructions and receive patient 12 information at any location.

In some examples, clinician module 16 may also include a memory for storing data. For example, in some examples, the memory may store information related to patient 12, e.g., health information, sensed physiological parameters, historical condition data, prescription information, or other information related to clinician 15 such as identification information. In some examples, the memory may also store other data that may be useful in managing the medical condition of patient 12. The memory can include any suitable type of memory, such as RAM, ROM, PROM, EPROM, EEPROM, flash memory, a hard disk, a CD-ROM, a floppy disk, a cassette, magnetic media, optical media, or other computer readable media.

Clinician interface 26 can be any user interface suitable for interaction with clinician 15. For example, clinician interface 26 may include a display and one or more input buttons that allow another component of system 10 to receive input from clinician 15. Alternatively or additionally, clinician interface 26 may utilize a touch screen display. The screen may be a LCD, dot matrix display, OLED display, touch screen, or any other device capable of delivering and/or accepting information. For visible indications of information, a display screen may suffice. For audible and/or tactile indications of information, clinician interface 26 may further include one or more audio speakers, voice synthesizer chips, piezoelectric buzzers, or the like.

Input buttons for clinician interface 26 may include a touch pad, increase and decrease buttons, emergency shut off button, and other buttons that may control or modify a therapy delivered to patient 12, as well as other buttons for inputting information into clinician module 16. A processor of system 10 may control clinician interface 26, retrieve data stored in a memory of system 10, store data within a memory of system 10, and/or transmit data from clinician module 16 to another module of system 10.

Therapy module 18 may include any components and configuration suitable for storing the therapy instructions that associates patient conditions with the one or more therapy regimens used to treat patient 12, and providing remote access to the stored therapy instructions. For example, in some examples, therapy module 18 includes a memory (i.e., one or more memories) for storing the preset patient conditions detectable based on a physiological parameter sensed by sensor 22. These patient conditions may be ranges for specific physiological parameters sensed by sensor 22 or some other function of sensor 22 output. The memory may also store a plurality of therapy regimens of the therapy instructions. Each therapy regimen may be a specific set of medications, doses, and delivery times.

In some examples, the plurality of stored therapy regimens may not merely include predetermined prescriptions that are each associated with a condition. Instead of or in addition to a predefined prescription that is associated with a respective condition, the plurality of stored therapy regimens may be defined by an equation or algorithm that indicates a prescription that is a function of the detected condition. For example, the dosage, intake times, and/or medications of each prescription may be generated based on the detected condition, e.g., the contingent prescriptions may be one prescription that varies based on the condition, and the stored equation or algorithm. In this fashion, clinician 15 may not need to create a large table of condition-therapy regimens associated with each condition.

In one example, an algorithm for selecting a therapy regimen includes monitoring a physiological parameter of patient 12 and determining whether the patient condition has been stagnant for a particular time range (e.g., the past day, days or week). If the patient condition is stagnant (e.g., the determined patient condition has not changed), the algorithm may include modifying the current therapy regimen in a manner that may help improve the patient condition (e.g., change the current patient condition). The algorithm may implement rules for modifying the current therapy regimen, such as increasing a dosage of a particular medication or adding a medication to the therapy regimen. The rules may be, for example, determined by clinician 15 in some examples. As an example of this type of algorithm, therapy module 18 can automatically monitor a physiological parameter of the patient, and determine, based on past physiological parameter data, whether the patient condition is improving (e.g., approaching a normal pulmonary pressure over time). If the physiological parameter indicates the patient condition is not improving, therapy module 18 can implement a therapy regimen that may help improve the patient condition (e.g., by selecting the therapy regimen from a plurality of stored therapy regimens or by adjusting the current therapy regimen based on a set of stored rules).

In another example, rather than implementing an algorithm to vary a therapy regimen based on historical patient condition data (e.g., a pattern in the patient condition over time), therapy module 18 can adjust a therapy regimen based on therapy regimens associated with a detected patient condition pattern. For example, clinician 15 can define a patient condition as including a time component (e.g., a high pressure detected for a certain number of hours or days), and associate a therapy regimen with the patient condition. In this way, therapy module 18 can select a therapy regimen based on a patient condition determined over the course of one or more days, rather than an instantaneous patient condition.

In addition to a memory, therapy module 18 may include a processor that can execute therapy instructions by automatically selecting a therapy regimen based on a patient condition detected based on a physiological parameter sensed by sensor 22. In some examples, therapy module 18 may include one or more databases for storing therapy instructions, historical condition data, therapy regimens, or any other information used by system 10 to monitor and treat patient 12.

In some examples, patient module 14, clinician module 16, and algorithm module 18 may be located remotely from one another. For example, in some examples, one or more of patient module 14, clinician module 16, and algorithm module 18 may be provided in different locations. As one example, patient module 14 may be located in the home of patient 12, clinician module 16 may be located in a medical care facility, e.g., a clinic or a hospital, and therapy module 18 may be located in an external server at a separate server facility. In another example, therapy module 18 and patient module 14 may be located in a device within the home of patient 12, while, in other examples, therapy module 18 and clinician module 16 may be located in the same medical care facility. In still other examples, two or more of the modules of system 10 may even be located within the same device (e.g., a patient programmer carried by patient 12). As these examples illustrate, patient module 14, clinician module 16, and therapy module 18 may be located in any configuration that facilitates the monitoring and treatment of patient 12.

Patient module 14, clinician module 16, and therapy module 18 may communicate with one another via network 20 when located remote from one another. In some examples, network 20 includes one or more of a local area network (LAN), wide area network (WAN), public switched telephone network (PSTN), or cellular telephone network. One or more components of patient module 14, clinician module 16, and therapy module 18 may be configured to connect to network 20 in order to transmit and receive information between modules 14, 16, and 18.

In general, clinician module 16 receives input from clinician 15 to define the therapy instructions used by therapy module 18 to select the appropriate therapy regimen, e.g., contingent medication prescription. In some examples, the therapy instructions may include additional instructions to monitor multiple conditions of patient 12. For example, clinician 15 may define other instructions, or algorithms that therapy module 18 may use to automatically monitor patient 12. That is, clinician 15 may initially provide input to define each of the instructions, or algorithms, that allow therapy module 18 to subsequently monitor and treat the patient 12 with minimal interaction from clinician 15 otherwise required.

Sensor 22 of patient module 14 may sense a physiological parameter of patient 12 that can be used to detect a condition of patient 12, which is then used to determine a therapy regimen for patient 12. The output of sensor 22 can be an electrical signal that is directly representative of the physiological parameter, such as a pressure or impedance. Therapy module 18 (or another module of system 10) may detect a condition of patient 12 when the physiological parameter correlates with the condition, e.g., as indicated by stored data that defines a condition. For example, clinician 15 may set a physiological parameter value range for each condition, and each condition is then detected when sensor 22 senses a physiological parameter value that correlates to that condition. In other examples, one or more sets of therapy instructions may be used to correlate sensed parameters to each of the conditions. As described with respect to FIG. 2, the therapy instructions may include, for example, a set of instructions for detecting a specific pressure range and a set of instructions for detecting a specific change in pressure. In other examples, sensor 22 may implement a portion of the therapy instructions so that sensor 22 identifies the condition based on the sensed physiological parameters.

As described herein, each condition may be associated with a therapy regimen designed to treat patient 12. Because sensor 22 may sense different types of physiological parameters in some examples, each condition may be varying degrees of one type of physiological parameter and varying degrees of another type of a different physiological parameter. For example, each condition may relate to different blood pressure states, different trans-thoracic impedances, or even different combinations of these two measurements.

Figure 2:
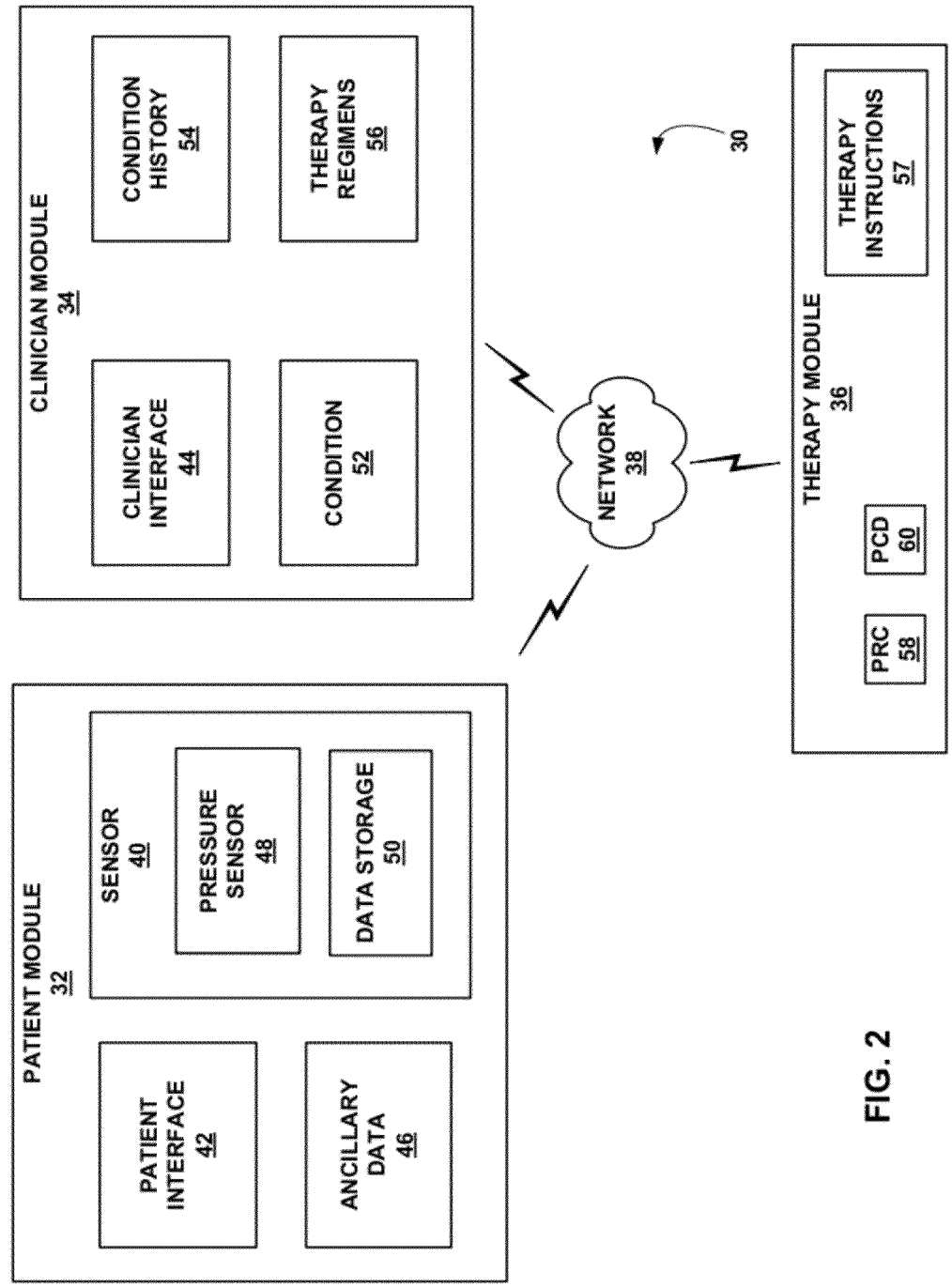
FIG. 2 is a conceptual diagram of an integrated patient care system for monitoring and treating congestive heart failure of a patient.
Figure 3:
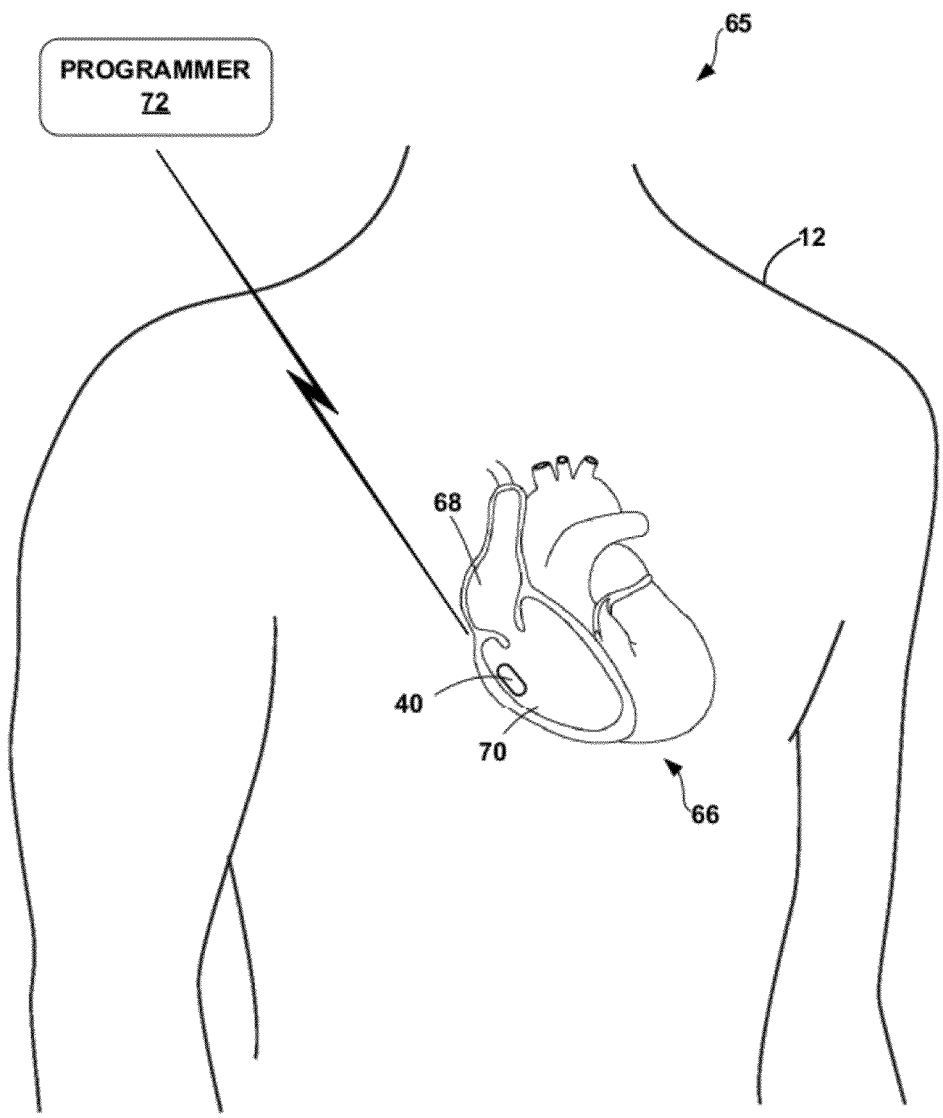
FIG. 3 is a conceptual diagram illustrating an implanted sensor for sensing a condition of a patient.

In one example of sensor 22, as discussed in further detail with respect to FIGS. 2 and 3, may be configured and positioned relative to patient 12 to sense right ventricular pressure (i.e., one type of a physiological parameter) of patient 12. In some examples, right ventricular pressure may be used in place of pulmonary artery pressure because the two pressures can be roughly equivalent when the pulmonary valve is open during right ventricular contractions. As discussed in further detail below, pulmonary artery pressure may be used as an indicator of the progression of congestive heart failure of patient 12. Therefore, therapy module 18 may detect a pulmonary artery pressure severity condition based on the sensed right ventricular pressure from sensor 22. For example, each condition may relate to a pressure range defined by the therapy instructions (e.g., very low pressure, low pressure, normal pressure, high pressure, and very high pressure). Pulmonary artery pressure can be used to define five different conditions for patient 12 in this example. Each condition may also indicate a certain risk for HF, e.g., conditions of higher pulmonary pressure indicates more thoracic fluid volume and/or more stress on the right ventricle of the heart.

Sensor 22 may sense physiological parameters indicative of the condition continuously, periodically, or in response to any event and transmit an indication of the sensed parameters to clinician module 16 or therapy module 18 as required for management of the medical condition (e.g., HF). Although sensor 22 may sense a physiological parameter that is indicative of the condition of patient 12, the actual detection of the condition by system 10 may not occur at sensor 22. For example, patient module 14 may include a processor that receives the output, e.g., a physiological parameter, from sensor 22 and determines, based on the sensor output, whether the patient condition is detected. As another example, patient module 14 may transmit the sensed physiological parameter to therapy module 18, which may then detect the patient condition. Therapy module 18 may then correlate the sensed physiological parameter to one of the conditions associated with the therapy instructions. In other examples, clinician module 16 may detect the patient condition based on the output from sensor 22.

In any case, sensor 22 may directly or indirectly detect the specific condition. When matching the sensed physiological parameter to one of the conditions, the therapy instructions may use a condition identifier having addition instructions or equations for identifying the condition from the physiological parameter. In one example, the conditions identifiers may be a pressure range check instruction, a pressure change detection instruction, or a patient pressure status instruction.

In some examples, clinician module 16 displays medical information of patient 12 via clinician interface 26. Clinician 15 may review the medical information displayed on clinician interface 26 and provide input that defines the therapy instructions, e.g., the conditions or condition identifiers, used to monitor the progression or regression of patient 12. In addition, clinician 15 may provide input to clinician interface 26 defining a plurality of therapy regimens that may be transmitted to patient module 14 for presentation to patient 12. The therapy regimens may be contingent prescriptions for a certain therapy. In other words, clinician 15 may load any number of therapy regimens into the therapy instructions such that each therapy regimen is contingent upon an associated condition being detected from patient 12.

In one example, the therapy regimens may be contingent medication prescriptions that instruct patient 12 to take certain medication, the appropriate dose of the medication, and the time for taking each medication. In some examples, therapy regimens may include instructions for patient 12 to assume certain postures, assume certain positions or undertake certain activities, or even to contact another healthcare professional. In some examples, the therapy regimens may include instructions for implementation by patient 12 for activating, deactivating, or otherwise modifying one or more medical devices used to manage the detected condition. In other examples, the therapy regimens may include instructions that command one or more components of patient module 14 to automatically titrate a therapy, e.g., electrical stimulation therapy or drug delivery, for treating the medical condition of patient 12. It is noted that the therapy regimens included in the therapy instructions defined by clinician 15 may included any of these types of therapies at the same time. For example, the therapy instructions for patient 12 may include both therapy regimens of medications and adjustments to medical devices. Other types of therapy regimens are contemplated.

In some examples, clinician module 16 receives medical information related to patient 12 from one or more components of patient module 14. For example, patient module 14 may store medical information related to patient 12, such as medical history information of patient 12, historical or real-time physiological parameters (e.g., sensed data by sensor 22) of patient 12, detected conditions, feedback from patient 12 related to previously implemented therapy regimens, and the like, and transmit the medical information to clinician module 16 via network 20. Upon receiving the medical information, clinician module 26 may display the information via clinician interface 26 such that clinician 15 can review the information. Clinician 15 may review this information, or portions of this information, and create a therapy plan specific to patient 12.

In other examples, clinician module 16 may provide medical information from other patients. Clinician 15 may then use this information from other patients to identify those therapy regimens effective in treating conditions similar to the ones of patient 12. This other patient information may be from patients treated by clinician 15, a clinic in which clinician 15 practices medicine, or even remote patients with information included in an accessible database.

Based upon reviewing the medical information of patient 12, clinician 15 may provide input via clinician interface 26 defining the therapy instructions. This input may specify the parameters of condition identifier algorithms, specific conditions, or even the therapy regimens for each of the conditions detectable based on a physiological parameter sensed by sensor 22. As described above, the condition identifiers may define how to relate sensed physiological parameters to one of the conditions, e.g., by associating specific physiological parameter values with a specific patient condition. The input from clinician 15 may also define associations between each of the conditions and a therapy regimen for patient 12 when the condition is detected. In other words, the input provided by clinician 15 may indicate a correlation between particular conditions of patient 12 and particular treatment regimens that, according to clinician 15, may most effectively treat the detected condition of patient 12.

Clinician module 16 may subsequently transmit the therapy instructions received via clinician interface 26 to therapy module 18 so that therapy module 18 may automatically select the therapy regimen associated with patient condition detected based on the physiological parameter sensed by sensor 22. In some examples, clinician module 16 may only transmit changes in the therapy instructions to therapy module 18. In other words, clinician module 16 may keep a copy of the therapy instructions stored at therapy module 18 and look for changes made to the therapy instructions by clinician 15. Clinician module 16 may then only transmit the recognized changes to the therapy instructions as an update to the previously existing therapy instructions.

Upon acquiring the therapy instructions from clinician module 16, therapy module 18 may be capable of monitoring and treating patient 12 by automatically selecting a therapy regimen based on a detected patient condition. For example, a processor of therapy module 18 may analyze physiological parameters received from sensor 22 and determine, based on the analysis of one or more physiological parameters with a condition identifier, whether the patient condition has been detected. Therapy module 18 may then automatically select a therapy regimen associated with the detected condition and transmit the selected therapy regimen to patient module 14. Therapy module 18 may perform the automatic selection at any time predefined by clinician 15, as requested by patient 12, or otherwise required by circumstances surrounding patient 12. In this manner, system 10 may effectively treat patient 12 in more responsive manner than possible with manual observation and therapy updates. In other examples, patient module 14 or clinician module 16 may automatically select the therapy regimen based on the detected condition. Any module of system 10 may select the therapy regimen according to therapy instructions.

Therapy module 18 may transmit the selected therapy regimen to patient module 14 via network 20. In some examples, patient module 14 displays the therapy regimen on patient interface 24 for review by patient 12. The therapy regimen may include written instructions instructing patient 12 to modify an aspect of one or more therapies designed to treat or minimize the medical condition of patient 12. For example, the therapy regimen may include instructions for patient 12 to alter a dosage, frequency, time, etc. of taking a medication that is used to treat the medical condition of patient 12. In this example, the therapy regimen may include a contingent medication prescription. In some examples, the therapy regimen set may instruct patient 12 to contact clinician 15 or another clinician based on the detected condition of patient 12. In examples in which patient module 14 includes a therapy delivery component or device, e.g., an implantable medical device (IMD) or external device that delivers therapy to patient 12, the therapy regimen may include an adjustment to the therapy program implemented by the device. Patient 12 may need to manually adjust one of the parameters of the therapy program or patient module 14 may automatically upload the updated therapy program to the device. Patient 12 may still be notified of such an automatic update to the therapy program.

Many examples herein, such as the examples illustrated in FIGS. 2 and 3, are described with respect to patient 12 suffering from congestive heart failure (HF) and integrated patient care system 30 (of FIG. 2) configured to monitor and treat the congestive heart failure of patient 12. However, as discussed, in other examples, patient 12 may suffer from another medical problems or circumstances that may benefit from an integrated patient care system configured to monitor and treat patient 12.

FIG. 2 is a schematic illustration of integrated patient care system 30, which is configured to monitor and treat congestive heart failure of patient 12. System 30 of FIG. 2 may be substantially similar to system 10 of FIG. 1. As illustrated in the example of FIG. 2, system 30 generally includes patient module 32, clinician module 34, and therapy module 36, in addition to network 38 via which patient module 32, clinician module 34, and therapy module 36 communicate with one another. In the example illustrated in FIG. 2, for monitoring and providing therapy for congestive heart failure, patient module 32 includes sensor 40, patient interface 42, and ancillary data 46. Clinician module 34 includes clinician interface 44, condition module 52, condition history module 54, and therapy regimens module 56. Therapy module 36 includes therapy instructions module 57, pressure range check (PRC) instruction module 58 and pressure change detection (PCD) instruction module 60.

Patient module 32 may be substantially similar to patient module 14 (FIG. 1) and may be configured as a component of integrated patient care system 30. Patient module 32 includes patient interface 42 that includes a display to present information to patient 12 and one or more devices that receive input from patient 12. Patient module 32 also includes sensor 40 that is configured to sense right ventricular pressure of patient 12, which may be used to monitor the congestive heart failure of patient 12. Sensor 40 of FIG. 2 includes pressure sensor 48 and data storage 50. In other examples, sensor 40 may include a separate processor or other components used to detect a condition of patient 12.

In the example of FIG. 2, pressure sensor 48 is configured and positioned within patient 12 to sense pressure in the pulmonary artery of patient 12, which may be used to monitoring the severity, or degree, of congestive heart failure of patient 12. Sensor 40 includes data storage module 50 which may be a memory that stores data related to the sensed pressure parameter from pressure sensor 48. Data storage 50 may include the raw output from pressure sensor 48, the calibrated pressure that was sensed, or even the condition detected from the sensed pressure in some examples. Data storage 50 may also store a time stamp of when the pressure was sensed and other operational data related to pressure sensor 48. Patient module 32 also includes ancillary data module 46 that may sense and/or store ancillary data of patient 12. Ancillary data may be any data indicative of the general health or information of patient 12. For example, in some examples, ancillary data may include data related to the vital signs of patient 12, e.g., body temperature, respiration rate, heart rate, and blood pressure of patient 12. In other examples, ancillary data 46 may store information regarding the activity of patient 12, postures of patient 12, or any other data. Therefore, ancillary data 46 may include a memory for storing the ancillary data and/or one or more sensors that generate the ancillary data.

Patient interface 42 may be substantially similar to patient interface 24 (FIG. 1), and may be useful for displaying or presenting information to patient 12. For example, patient interface 42 may present one or more therapy regimens selected by therapy module 36, instructions with which patient 12 may implement the selected therapy regimen, e.g., to take a particular dosage of medication at a particular time of day for managing the congestive heart failure of patient 12. In other examples, patient interface 42 may be used to receive feedback from patient 12 regarding any aspects of the distributed therapy regimen or associated features of system 30. For example, patient interface 42 may prompt patient 12 to provide feedback indicative of one or more side effects related to the selected therapy regimen, a rating related to the effectiveness of the selected therapy regimen, health history information that may be useful to clinician 15 for managing the congestive heart failure of patient 12, or any other information related to the treatment of patient 12.

In the example shown in FIG. 2, pressure sensor 48 senses a physiological parameter used to detect a condition of patient 12. In the example of FIG. 2, the sensed physiological parameter is pulmonary artery pressure and the condition is a level of the pulmonary artery pressure. Although the examples described herein relate to detecting pressure states, e.g., which are conditions of patient 12 in this example, from sensed pulmonary artery pressures of patient 12, patient module 32 may detect pulmonary pressure states from other sensed physiological parameters or different conditions from one or more physiological parameters in some examples. In other examples, patient module 32 may detect several different types of conditions at the same time. In this example, patient module 32 may detect a posture condition and a pulmonary artery pressure to provide a more complete indication of patient 12 symptoms. In any case, sensor 40 may detect a condition of patient 12 for selecting a therapy regimen previously prescribed by clinician 15 contingent upon the detection of the condition.

A pulmonary artery pressure level may be an appropriate condition to be used an indicator of the status of the congestive heart failure of patient 12. Because congestive heart failure may result in accumulation of fluid in the lungs of patient 12, e.g., pulmonary edema, pulmonary artery pressure may increase when heart failure becomes more severe. Progression of congestive heart failure, therefore, may be indicated by increasing pulmonary artery pressures. Since pulmonary artery diastolic (PAD) pressure may be correlated to left ventricular filling pressure, an elevated PAD pressure may indicate a high level of fluid within the lungs of patient 12 and potential cardiac problems. For example, an elevated PAD pressure may indicate excess stress on the right ventricle and potential right ventricle enlargement. In addition, an elevated PAD pressure may indicate that the left ventricle may become enlarged such that the expanded cardiac muscle is limited in its ability to maintain sufficient systemic blood flow levels. Once the heart is unable to maintain appropriate systemic blood flow, tissues and organs may lose their ability to obtain oxygen, among other chemical transport needs.

Pressure sensor 48 or, more generally, sensor 40, may measure the pulmonary artery pressure of patient 12 in any suitable manner. In some examples described herein, sensor 40 is implanted within the right ventricle of patient 12 (e.g., as illustrated in FIG. 3) to measure the right ventricular pressure of patient 12. The right ventricular pressure may subsequently be used to derive an estimated pulmonary artery diastolic (ePAD) pressure for patient 12. In other words, sensor 40 may still detect the pulmonary artery pressure condition of patient 12. The ePAD pressure generally refers to the measure of right ventricular pressure at the time the change in the pressure signal over time (dp/dt) is at a maximum. In some examples, as discussed in further detail in commonly-assigned U.S. Patent Application Publication No. 2009/0299198 by Carney et al., filed on May 20, 2008, entitled "ESTIMATING PULMONARY ARTERY DIASTOLIC PRESSURE," and herein incorporated by reference in its entirety, sensor 40 may determine an approximate time at which the pulmonary artery valve of patient 12 opens based on the right ventricular pressure in order to estimate the pulmonary artery diastolic pressure. In other examples, sensor 40 may determine ePAD pressure values for patient 12 in another suitable manner. For example, sensor 40 may be an ultrasound sensor implanted on the pulmonary artery to monitor flow and estimate the diastolic and even systolic pressures within the pulmonary artery.

An increase in ePAD pressure values may indicate that the congestive heart failure of patient 12 has worsened. For example, as discussed above, an increase in fluid in the lungs of patient 12 may be indicative of increased severity of the congestive heart failure, and may accordingly cause an increase in ePAD pressure values. Consequently, an increase in ePAD pressure values may be indicative of increased severity of the congestive heart failure. Conversely, a decrease in ePAD pressure values may signify the congestive heart failure condition of patient 12 has improved, e.g., a currently or previously implemented therapy regimen has reduced the amount of fluid within patient 12 lungs and/or dilated the blood vessels of patient 12.

In other examples, sensor 40 may be used to monitor the severity of heart failure by measuring a physiological parameter other than pulmonary pressures. For example, sensor 40 may include one or more electrodes used to measure a trans-thoracic impedance (which may also be referred to as intrathoracic impedance in some cases) of patient 12. When there is more fluid within patient 12, e.g., indicating pulmonary edema, the measured, or sensed, trans-thoracic impedance may decrease. In some cases, this trans-thoracic impedance may be used as a substitute for pulmonary artery pressures. The trans-thoracic impedance may be sensed by measuring the impedance of an electrical path between two electrodes, or combinations of multiple electrodes, at different locations with respect to the chest of patient 12. The electrodes may have different configurations to measure the impedance.

As examples of electrode configurations, both electrodes may be implanted within patient 12, both electrodes may be attached to the external skin surface of patient 12, or one electrode may be implanted and one electrode may be external. In a specific example, the electrodes already implanted within the patient when patient 12 has an implanted pacemaker, cardioverter and/or defibrillator or another medical device can be used to determine trans-thoracic impedance of patient 12. For example, a coil electrode within the heart and the housing electrode of the implantable medical device may be used an implanted electrodes to measure the trans-thoracic impedance. In this manner, patient module 32 may communicate with the implanted medical device in some examples to detect a patient condition. In another example, patient 12 may wear surface electrodes attached to the chest and electrically coupled to an external medical device that measures the impedance between the surface electrodes. In other examples, sensor 40 may be any sensor capable of detecting one or more conditions indicative of heart failure severity.

Data storage module 50 of sensor 40 may include one or more memory components that may, in some examples, store pressure measurement values sensed by pressure sensor 48. The memory can include any suitable type of memory, such as RAM, ROM, PROM, EPROM, EEPROM, flash memory, a hard disk, a CD-ROM, a floppy disk, a cassette, magnetic media, optical media, or other computer readable media. In some examples, patient module 32, clinician module 34, or therapy module 36 may access the stored data in data storage module 50 to detect the patient condition. In other examples, data storage 50 may only be used as temporary storage that is periodically transmitted to therapy module 36 via network 38.

Clinician module 34 may be substantially similar to clinician module 16 (FIG. 1) and may be configured as a component of integrated patient care system 30. Clinician module 34 includes clinician interface 44 for displaying information to and receiving input from clinician 15 and historical condition information in condition history 54. Condition history 54 may store previously collected physiological parameters and/or detected conditions of the pulmonary artery pressure of patient 12. For example, condition history 54 may include a memory that stores data for illustrating previous trends in the pulmonary artery pressure of patient 12. The memory can include any suitable type of memory, such as RAM, ROM, PROM, EPROM, EEPROM, flash memory, a hard disk, a CD-ROM, a floppy disk, a cassette, magnetic media, optical media, or other computer readable media. In addition, clinician module 34 includes condition module 52 and therapy regimen module 56. Together, condition module 52 and therapy regimen module 56 may provide therapy instructions 57 stored by therapy module 36. Therapy module 36 may use therapy instructions 57 to select the appropriate therapy regimen based on the detected condition. In other words, in some examples, clinician 15 may associate one or more conditions 52 with a therapy regimen of therapy regimens 56. This association may be transmitted to therapy module 36 and stored as therapy instructions 57.

The criteria with which each condition is detected from the sensed physiological parameters may also be determined by clinician 15. These criteria may also be referred to as condition identifiers because they identify how each condition is detected. In the example of FIG. 2, clinician 15 may select from three different criteria (also referred to as condition identifiers) for determining the condition of patient 12: pressure range, pressure change, and both pressure range and pressure change. Pressure range check (PRC) instruction module 58 of therapy module 36 associates each of a plurality of patient conditions with a range of values for the sensed physiological pressure. Pressure change detection (PCD) instruction module 60 of therapy module 36 associates each of a plurality of patient conditions with a threshold value for a change in pulmonary artery pressure. The different parameters (e.g., the range of values for a sensed physiological parameter associated with a respective condition or a threshold value for PCD associated with a respective condition) of each condition identifier may be stored as conditions 52 of clinician module 34.

Therapy instructions 57 may include PRC module 58 and PCD module 60 in other examples, and therapy instructions 57 may define parameters of each module 58 and 60. In other examples, therapy instructions 57 may include other modules that perform other functions defined by therapy instructions 57. For example, a condition state module may use the output from one or both of modules 58 and 60 to detect the condition from sensed physiological parameters. In another example, a patient therapy module may contain the associations between each condition and therapy regimens.

In some examples, clinician 15 may select which one of the condition identifiers (e.g., pressure range or pressure change) should be used to detect the patient conditions stored in therapy instructions 57. In other examples, clinician 15 may require that conditions are only detected when two condition identifiers (e.g., pressure range check and pressure change detection) indicate conditions associated with the same therapy regimen. In this manner, therapy module 36 may confirm the patient condition before releasing a contingent prescription from therapy instructions 57.

Clinician interface 44 may be substantially similar to clinician interface 26 (FIG. 1), and may display information to clinician 15 and receive input related to generating or updating therapy instructions 57. Clinician interface 44 may include a display that presents historical conditions from condition history 54, conditions to be detected from patient 12, and therapy regimens. In turn, clinician interface 44 may receive input from clinician 15 that sets the parameters of conditions 52, generates contingent prescriptions as therapy regimens 56, or other instructions related to the monitoring and treatment of patient 12. Clinician module 34 may then transmit updated therapy instructions 57 to therapy module 36 when clinician 15 is finished.

As described herein, therapy module 36 may transmit the parameters (e.g., threshold values or other values used to identify a patient condition) of one or more condition identifiers to clinician module 34 for review, and, in some cases, modification. In the example shown in FIG. 2, the condition identifiers are stored as PRC instruction module 58 and PCD instruction module 60. For each condition identifier 58, 60, clinician interface 44 may present the parameters to clinician 15 and clinician 15 may review how each parameter of the condition identifier is correlating to the historical condition data from sensor 40. For example, clinician interface 44 may present parameters of the PRC condition identifiers for identifying conditions, where the parameters include physiological parameters associated with a respective patient condition. Physiological parameter data may be presented in conjunction with the condition identifier parameters, and clinician 15 may adjust one or more condition identifier parameters to adjust when the physiological parameters indicate each condition is detected. This relationship between condition identifier parameters and physiological parameters of historical conditions is further illustrated below in FIG. 6.

In other examples of FIG. 2, therapy module 36 may use a different technique other than stored therapy instructions 57 to detect conditions and select a therapy regimen based on the detection. For example, in some examples, the physiological parameters, e.g., pulmonary pressure, may be transmitted from sensor 40 and patient module 32 to therapy module 36 via network 38. Therapy module 36 may determine the patient condition indicated by the sensed physiological parameters based on the received physiological parameters and condition identifiers 58 and 60. For example, therapy module 36 can determine a pressure state of patient 12 indicated by the sensed physiological parameters by comparing the sensed physiological parameters to the range of the pressure range parameters stored as PRC 58 and a detected pressure change value stored as PCD 60. Therapy module 36 can then select the appropriate therapy regimen based on the detected pressure state. In this manner, therapy module 36 may operate differently than a single look-up table or formula because multiple criteria may be used to determine the patient condition. Of course, clinician 15 may be able to configure each parameter of the modules used in this method to customize the detected conditions and therapy regimens for patient 12.

FIG. 3 illustrates a portion of a patient module 34 that includes sensor 40 implanted within right ventricle 70 of heart 66 in patient 12. As shown in the example of FIG. 3, system 65 includes sensor 40, a wireless pressure sensor attached to the chamber wall within right ventricle 70. Sensor 40 may be implanted with an intravenous lead and secured at a location within right ventricle 70 that does not interfere with normal contractions of right ventricle 70. In examples in which sensor 40 includes a wireless sensor 40, sensor 40 may include a power source, processor, telemetry module, and anything else required for sensor 40 to function. In this manner, programmer 72 may receive sensed pressures, e.g., physiological parameters, from sensor 40.

Sensor 40 may be configured to sense right ventricular pressure of patient 12 in the example of FIG. 3. As described herein, right ventricular pressure may be used to monitor the congestive heart failure condition of patient 12. Right ventricular pressure may be used to estimate the pulmonary artery diastolic pressure, and, accordingly, system 65 may detect the pressure condition of the pulmonary vasculature based on the right ventricular pressure. Other configurations and locations of sensor 40 within patient 12 may also be used. For example, in other examples, sensor 40 may be located on a lead that passes through right atrium 68 and also resides within right ventricle 70. For example, sensor 40 may be carried on a lead used by a pacemaker, a cardiac resynchronization therapy (CRT) device, cardioverter and/or defibrillator.

Programmer 72 may be configured to communicate with sensor 40, e.g., via wireless telemetry. Programmer 72 may be part of the patient module 32 used to monitor patient 12. Programmer 72 may, in some examples, transmit the pressures sensed by sensor 40 to therapy module 36, which may select a therapy regimen based on the patient condition detected based on the pressure sensed by sensor 40.

In other examples, physiological parameters of patient 12 may be sensed with other types of sensors or sensors placed in other location within or external to patient 12. For example, electrodes within or on patient 12 may be used to detect a trans-thoracic impedance condition. In other examples, temperature sensors, flow sensors, activity sensors, oxygen sensors, or any other sensors may be used to monitor patient 12 and select a therapy regimen.

Figure 4:
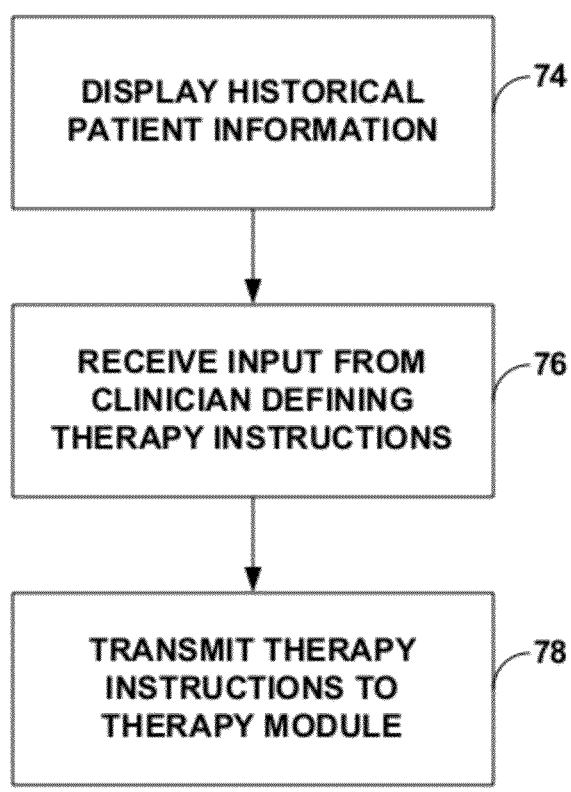
FIG. 4 is a flow diagram illustrating an example technique for receiving therapy instructions from a clinician.

FIG. 4 is a flow diagram of an example technique that may be performed by clinician module 16 (FIG. 1) to establish the therapy instructions used to detect patient conditions and select associated therapy regimens. As discussed with respect to FIG. 1, a clinician may provide input to define the therapy instructions used to monitor and treat patient 12. The therapy instructions may define one or more methods for determining how a patient condition is detected from sensed physiological parameters, one or more therapy regimens, and associations between therapy regimens and patient conditions. Because the therapy instructions may use one or more condition identifiers as at least part of an algorithm to detect the condition from the sensed physiological parameters, this input from clinician 15 may also establish parameters of these condition identifiers or when to use each condition identifier to detect the condition.

In the example technique illustrated in FIG. 4, clinician module 16 displays historical patient information of patient 12 via clinician interface 26 for review by clinician 15 (74). This historical patient information may include medical information of patient 12 or historical patient condition information (e.g., previously detected patient conditions, and the time and date of such detections). Upon reviewing this historical information, clinician 15 may provide input via clinician interface 26 to define the therapy instructions. In some examples, the historical patient information of patient 12 includes any one or more of detected patient conditions, sensed physiological parameters, patient 12 symptoms, or any other information related to the treatment of patient 12. Based on the historical information, a clinician may ascertain a historical pattern of pressures, which may help the clinician better understand the typical range of physiological parameter values a given patient might exhibit. The range limits or levels for thresholds used to determine a patient condition can then be selected in the context of the patient's historical values.

In one example, past pulmonary pressures may be presented to indicate any patterns or trends to a clinician. The historical patient information may also include the date of a previous heart failure decompensation. The clinician may then compare the pressures detected before and after the heart failure decompensation to adjust the ranges of pressures used by therapy module 18 to automatically select prescriptions and prevent future decompensation. The history pulmonary pressure values can indicate, for example, the pressure pattern leading up to the HF decompensation, such that the patient conditions can be defined to detect the pulmonary pressure pattern that indicates HF decompensation may occur.

Clinician module 16 receives the input provided by clinician 15, where the input indicates the parameters that define the therapy instructions used by therapy module 18 to detect conditions from sensed physiological parameters and/or select a therapy regimen transmitted to patient 12 (76). The therapy instructions includes a plurality of patient conditions and associated therapy regimens, and can also include the parameters (e.g., parameters of the condition identifiers) with which a patient condition is detected based on a sensed physiological signal. For example, clinician 15 may provide input regarding the thresholds of a pressure range check instruction used to detect each condition from the sensed physiological parameters. In some examples, clinician module 16 may review the clinician input and prompt clinician 15 to provide further input when the therapy instructions are incomplete, e.g., a condition is not associated with any therapy regimen. In other examples, clinician module 16 may require a confirmation from clinician 15 before the therapy instructions is completed and/or if clinician 15 inputs one or more parameters that are outside of generally used parameters (e.g., based on historical programming data for patient 12, clinician 15 or a plurality of patients or conditions).

Upon receiving input establishing the therapy instructions from clinician 15, clinician module 16 transmits the therapy instructions, which includes the detected conditions and associated therapy regimens, to therapy module 18 (78) in order to program therapy module 18. Once programmed, therapy module 18 may automatically select new therapy regimens for patient 12 upon the detection of conditions with sensor 22. Clinician module 16 may repeat the technique of FIG. 4 any time that clinician 15 desires to update or otherwise change the therapy instructions for patient 12.

Figure 5:
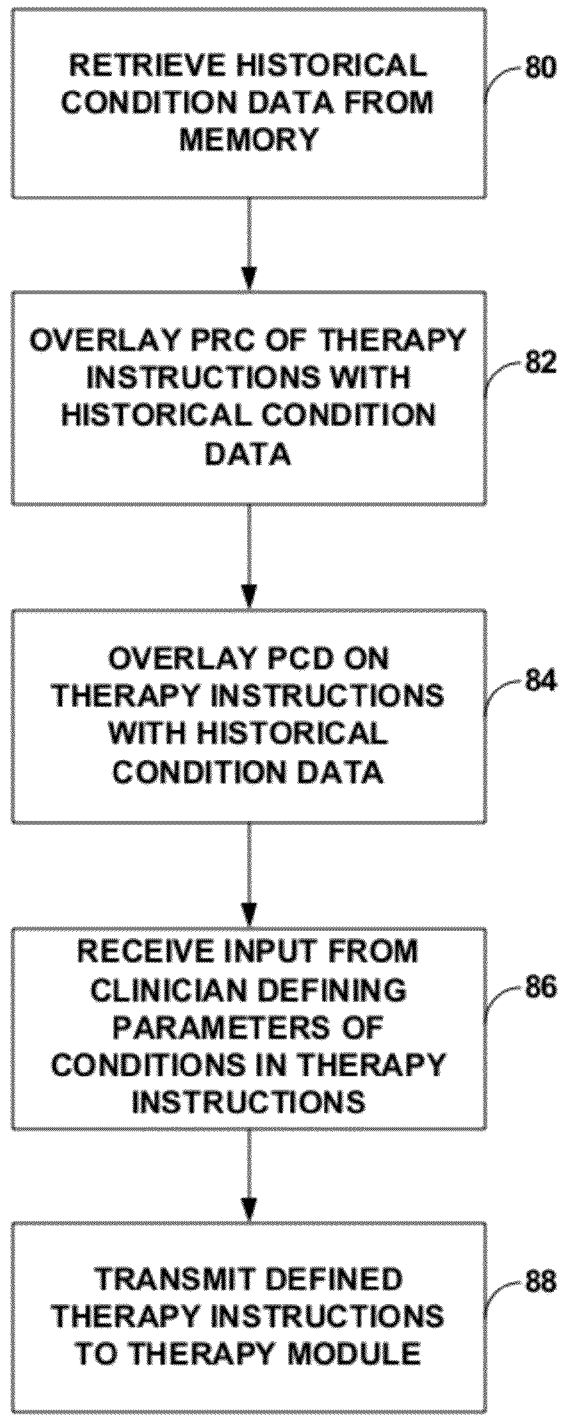
FIG. 5 is a flow diagram illustrating an example technique for displaying historical condition data and receiving therapy instructions from a clinician.

FIG. 5 is a flow diagram of an example technique that may be performed by clinician module 34 (FIG. 2) for associating patient conditions (which are a part of therapy instructions)

with parameters of the pressure range check (PRC) instruction 58, and the pressure change detection (PCD) instruction 60. Clinician module 34 may receive input from a clinician, e.g., clinician 15 (FIG. 1), via clinician interface 44. As shown in the example of FIG. 5, clinician module 34 retrieves the historical condition data from a memory (80), which can be a memory of clinician module 34 or another device, such as patient module 32 or therapy module 36.

Figure 6:
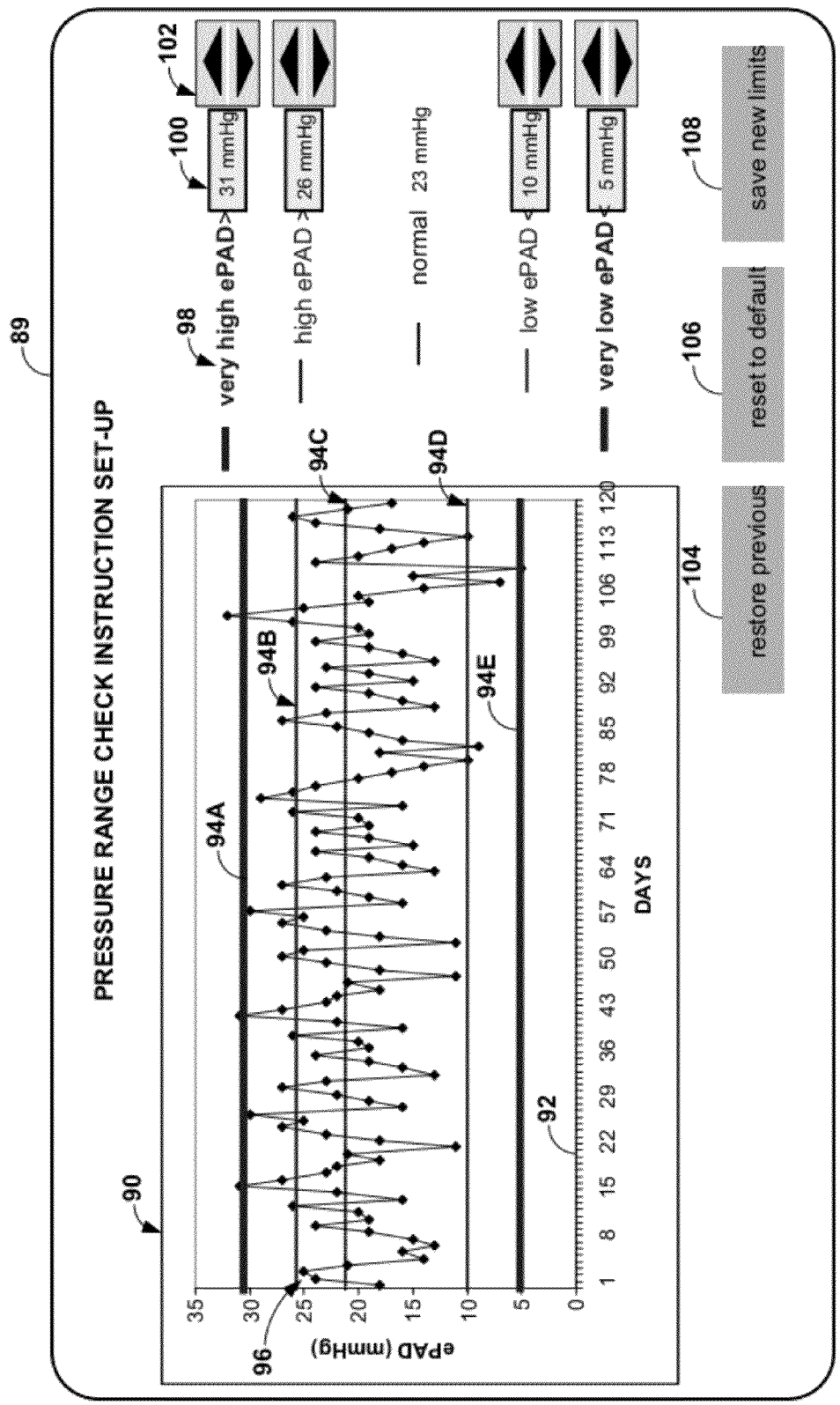
FIG. 6 is a conceptual diagram illustrating an example screen that may display historical condition data and receive therapy instructions from a clinician in the form of the pressure range check instruction.

Clinician module 34 then displays the historical condition data overlaid with the PRC instruction 58 parameters that define the physiological parameter range for each condition (82). For example, the pulmonary artery pressures previously sensed for patient 12 may be graphically presented and the parameters of PRC instruction module 58 may be graphically placed over the sensed parameters, as shown in the example of FIG. 6. Actual pulmonary artery pressures sensed for patient 12 overlaid with the parameters of the PRC instruction module 58 that are used to detect a patient condition can be a useful presentation of information with which clinician 15 may calibrate the parameters of the PRC instruction module 58 with data specific to patient 12. For example, a relatively high pressure pulmonary artery pressure for one patient may be a relatively low pressure for another patient. Thus, selecting parameters (e.g., pressure range thresholds) of the PRC instruction module 58 that are used to detect a patient condition can help customize an integrated patient care system to a specific patient 12. In addition, displaying actual pulmonary artery pressures values with the threshold ranges of the PRC instruction module 58 can provide an efficient display of data from which clinician 15 can relatively quickly ascertain the relevant pressure values.

Figure 17:
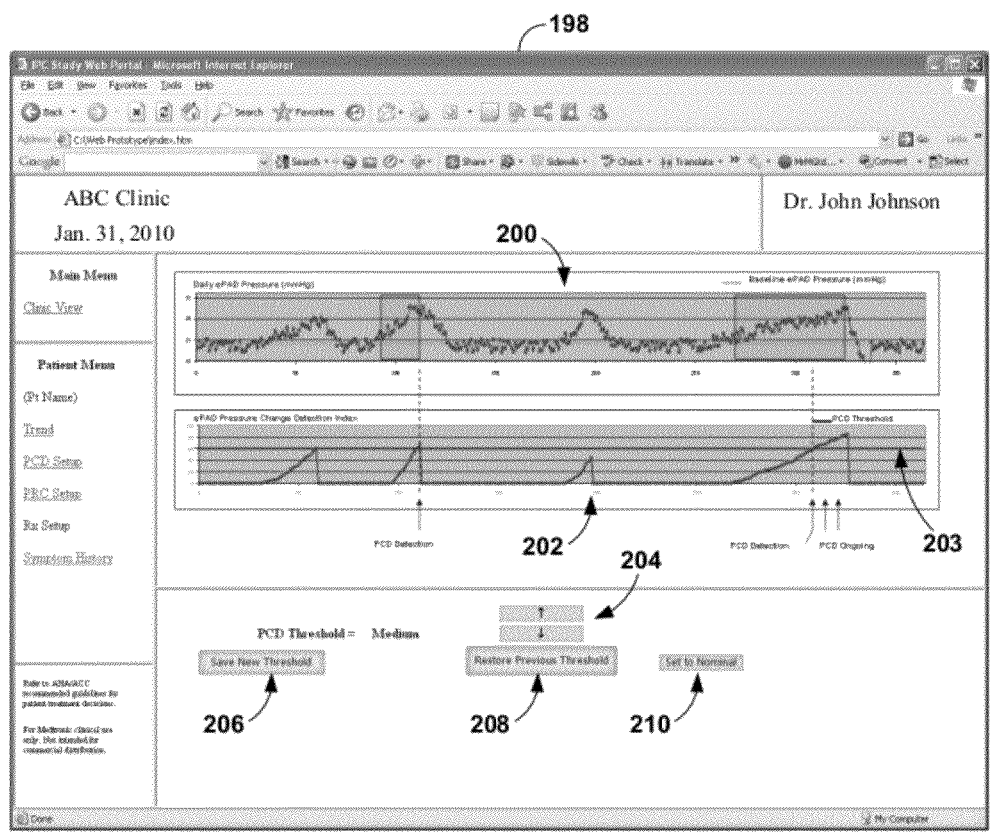
FIG. 17 is an example display that illustrates information related to detecting a patient condition based on a pressure change detection.

Clinician module 34 may also display the historical condition data overlaid with the PCD instruction 60 parameters (84). For example, the pressure changes sensed from patient 12 may be graphically presented and the parameters of PCD instruction 60 may be placed over the sensed parameters, such as shown in FIG. 17. As with pulmonary artery pressures, displaying the pressure values together with the parameters of the PCD instruction module 60 that are used to define patient conditions can be a useful presentation of information with which clinician 15 may calibrate the parameters of the PCD instruction module 58 with data specific to patient 12. For example, a specific change in pulmonary artery pressure for one patient can be relatively significant for one patient, but not for another. Thus, selecting parameters (e.g., pressure change thresholds) of the PCD instruction module 60 that are used to define patient conditions can help customize an integrated patient care system to a specific patient 12.

Clinician module 34, or clinician interface 44, may receive input from clinician 15 defining parameters of the patient conditions used in the therapy instructions (86). In other words, clinician 15 may provide input that adjusts the parameters of the PRC instruction module 58 and/or the PCD instruction module 60. Although clinician 15 may be able to provide input for each of the condition identifiers 58 and 60 on the same screen, other examples may require that clinician module 16 only present one of the condition identifiers at a time. Alternatively, if clinician 15 only uses one of the condition identifiers 58 or 60, clinician 15 may only view the parameters for the identifier used for the detection of the conditions from the sensed physiological parameters.

Once clinician 15 has defined the therapy instructions using the one or more condition identifiers, clinician module 34 may transmit the defined therapy instructions to therapy module 36. In some examples, the physiological parameter presented as the historical condition data may be pulmonary pressure or the estimated pulmonary artery diastolic (ePAD) pressure from sensing pressure in the right ventricle. However, the condition data may include other parameters or even more than one parameter on the same screen.

By showing historical condition data, clinician 15 may be able to review any trends in the condition of patient 12 useful in effectively treating heart failure. These trends may identify normal physiological activity, recent changes in patient 12, or other problems that may affect the definition of therapy instructions for further monitoring. In addition, clinician 15 may update the therapy regimens for each of the conditions defined in the therapy instructions. These therapy regimens may be similar to those discussed in more detail in FIG. 7.

FIG. 6 illustrates screen 89 that may be displayed by clinician interface 44 of clinician 15 module 34 of FIG. 2. In some cases, it may be useful to display at least part of a therapy instruction with historical physiological parameter data for patient 12 in order to provide context for clinician 15 to update or generate therapy instructions. As shown in the example of FIG. 6, screen 89 may present historical condition data, e.g., physiological parameters, to aid clinician 15 with the definition of parameters with which certain patient conditions can be detected using PRC instruction module 58 of therapy module 36. As discussed above with respect to FIG. 2, PRC instruction module 58 can be used to detect a patient condition based on a range of values for the sensed pulmonary artery pressure. Screen 89 includes graph 90, conditions 98, condition parameters 94, pressure parameter 100, range input 102, restore button 104, default button 106, and save button 108. A clinician may interact with screen 89 to define patient conditions that may later be detected based on the physiological parameters sensed by a sensor (e.g., sensor 22 in FIG. 1 or sensor 40 in FIG. 2).

Historical condition data 96 is displayed in graph 90 as daily ePAD pressures over time for the past three months. Axis 92 includes markings representative of the 120 days, and denotes the start of each week (e.g., each seven days), e.g., with a marking at each of day 1, day 8, day 15, day 22, etc. Very high state 94A, high state 94B, normal state 94C, low state 94D, and very low state 94E (collectively "condition parameters 94") are shown graphically as overlaid on the historical condition data. Condition parameters 94 include a range of ePAD pressures, and, in the example shown in FIG. 6, each range is defined relative to a normal pressure. A normal pressure can be, for example, a pressure that indicates heart 66 of patient 12 is functioning properly or at an acceptable level, e.g., as determined by clinician 15. For example, the normal pressure can be the pulmonary pressure when therapy for managing heart failure of patient 12 is relatively efficacious, such that the normal pressure can be a baseline pressure value for determining the relative medical condition of patient 12. The normal pressure can also be referred to as a "nominal" pressure in some examples.

As shown in FIG. 6, each of condition parameters 94 is numerically indicated by pressure parameters 100. Clinician 15 may interact with screen 89 via clinician interface 44 (FIG. 2) in order to modify condition parameters 94 and also change the corresponding pressure parameters 100. In the example shown in FIG. 6, very high state 94A is set to a threshold of greater than 31 mmHg, high state 94B is set to a threshold of greater than 26 mmHg (and less than or equal to 31 mmHg), normal state 94C is set to a range between 26 mmHg and 10 mmHg, low state 94D is set to a threshold less than 10 mmHg (and greater than or equal to 5 mmHg), and very low state 94E is set to a threshold lower than 5 mmHg.

Each of conditions 94 may be detected based a respective threshold pressure value. For example, as soon as the sensed ePAD exceeds (e.g., is greater than) a particular threshold, the corresponding condition may be triggered as detected. However, other examples may require that the sensed ePAD (or other physiological parameter value) exceeds a threshold for a specific amount of time. In some cases, the sensed physiological parameter value (ePAD or otherwise) that is compared to the threshold value may be the instantaneous physiological parameter value, a mean, median, peak or lowest value of the physiological parameter sensed within a particular duration of time (e.g., a few seconds, a minute, an hour, or the like), which may be selected by clinician 15.

In one example, the condition is only detected when the value of the sensed physiological parameter exceeds the threshold value for at least 24 hours. In another example, the condition is detected when the physiological parameter value exceeds the respective threshold for a predetermined number of days out of a total number of days, e.g., three out of five days. In this manner, condition detection may guard against sporadic measurements of the physiological parameter due to a patient or sensor anomaly.

Clinician 15 may adjust the physiological parameter values that define each of conditions 94 by using range input 102. For each of conditions 94 (other than normal state 94C in the example shown in FIG. 6, which can be predetermined and stored by clinician module 34), clinician 15 may select one of the arrows of range input 102 to move the threshold values up or down. In other examples, clinician 15 may be able to adjust normal state 94C. In this manner, clinician 15 may adjust the parameters of PRC instruction module 58. In some examples, as clinician 15 modifies the range of pressure values for each of the patient conditions, clinician module 34 may automatically update graph 90 such that lines 94A-94E associated with the patient conditions are at the adjusted threshold pressure values.

In other examples, screen 89 may provide different tools with which clinician 15 adjust the parameters that define each of the conditions 94. For example, in one example, clinician 15 may interact with graph 90 to change the parameters associated with each of the conditions 94. For example, clinician 15 may click on one of conditions 94 and drag the threshold value (indicated by the solid horizontal line in FIG. 6) to a desired value along the y-axis. In some examples, clinician 15 may click within graph 90 to zoom in or zoom out on the historical condition data 96. Once clinician 15 is satisfied with the ranges for each of conditions 94, clinician 15 may select save button 108. Upon selecting save 108, clinician 15 may be required to confirm the change and/or review the therapy regimens associated with each condition before the new therapy instructions are generated.

In addition to save button 108, screen 89 of clinician interface 44 may present additional buttons to aid clinician 15 with the condition defining process. Restore button 104 may revert the thresholds of conditions 94 to the previously saved states when selected by clinician 15. Default button 106, when selected, may reset each of conditions 94 to factory or general clinic thresholds of average patients.

Although the historical condition data and condition states are presented graphically, clinician interface 44 may present this same information is a textual or numerical format. Such formats may be preferred by some clinicians or required when presenting the information to a clinician on certain portable devices. For example, numerical data alone may be preferred if screen 89 is presented on a mobile device with limited graphical or networking abilities.

FIG. 7 is a schematic illustration of screen 110, which can be displayed by clinician interface 44. Clinician 15 may interact with screen 110 to provide input to establish therapy regimens for each of the conditions defined in FIG. 6 for the PRC instruction module 58. In other words, screen 110 may be a snapshot of the therapy instructions transmitted to therapy module 36 because it includes each condition detected based on ePAD values and the associated contingent medication prescriptions, e.g., therapy regimens. As illustrated in FIG. 7, clinician 15 may select one or more medications, dosages, quantities of medication, and iterations of medication intake, and associate the selections to a condition, or pressure range, of patient 12. Displaying the therapy regimens for each of the patient conditions in a common screen may provide an interface that allows clinician 15 to compare the treatments that are being recommended as a function of the pressure categories.

Interface display 110 includes condition column 112, medication column 114, dosage column 116, quantity column 118, iteration column 120, and alternate name column 122. Condition column 112 indicates the range of the condition as already defined, e.g., using screen 89 shown in FIG. 6. In some examples, screen 110 may allow clinician 15 to adjust the range of ePAD values used to define each condition. Medication column 114 may include a pull-down menu with all of the available medications from which clinician 15 can select for the contingent prescriptions. In some examples, clinician 15 may be able to write in desired medications or search for other medications not provided within the pull-down menu.

Each of dosage column 116, quantity column 118, and iteration column 120 provide input arrows to increment or decrement the values for each of the entries. Dosage column 116 provides the dosage for each medication (e.g., 50 milligrams), quantity column 118 indicates the number of pills or doses of each medication to take at a time, and iteration column 120 provides the number of times each number of doses needs to be taken by patient 12 each day. However, clinician 15 may also directly input the desired value. Alternative name column 122 may allow clinician 15 to provide an additional identifier for the medication prescribed in medication column 114. This additional identifier may be a common name or a way for patient 12 to differentiate between different medications that are prescribed in a therapy regimen. In the case of congestive heart failure, example medications that may be distributed to patient 12 via this contingent medication prescription may include diuretics, vasodilators, beta blockers, or any other medications to treat heart failure (or another medical condition).

In other examples, screen 110 may present therapy instructions in a different manner. For example, in another example, each condition of condition column 112 is associated with a text box in which clinician 15 may enter a respective therapy regimen. Screen 110 may provide a delete input and an edit input to allow clinician 15 to modify each of the therapy regimens. In another example, screen 110 provides a pop-up window that allows clinician 15 to modify a prescription, e.g., a medication, dosage, quantity, times per day, and alternative name, for defining the therapy regimen of each condition. In this manner, screen 110 may allow clinician 15 to define the therapy instructions using a wide variety of techniques.

In some examples, therapy regimens in screen 110 may include instructions for patient 12 other than medications. These other instructions may be postures that patient 12 should remain in to combat fluid retention, activities to try, or foods to avoid. In other examples, screen 110 may also include other specific instructions regarding one or more therapy regimens. These instructions may include a time of day to take each medication, whether the medication needs to be taken with food, or even side effects to watch for that indicate an adverse reaction to the therapy regimen. When a therapy regimen includes multiple medications, each medication may even have an order in which to take the medication.

If patient module 32 includes a delivery device, e.g., a pill dispenser, the therapy regimens displayed by screen 110 may be converted into digital instructions readable by the pill dispenser. If the therapy regimens are intended to control one or more medical devices, the therapy regimens may be formatted into the appropriate software before distribution.

Figure 8:
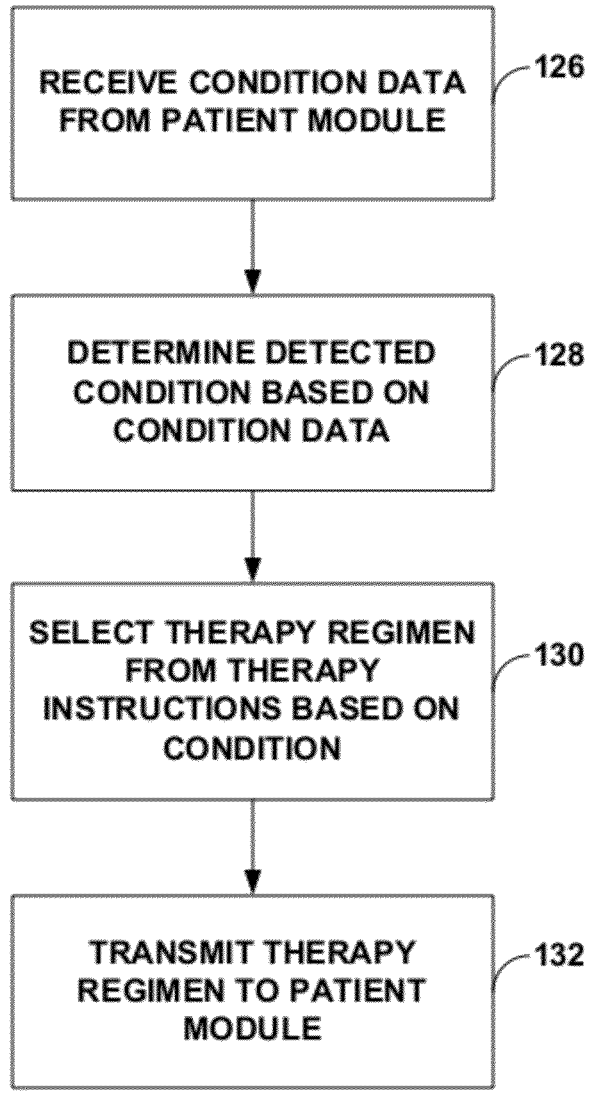
FIG. 8 is a flow diagram illustrating an example technique for selecting a therapy regimen from therapy instructions based on a detected patient condition.

FIG. 8 is a flow diagram of an example technique that can be performed to select and transmit a therapy regimen to patient module 14. Although FIG. 8 is described with respect to therapy module 18 (FIG. 1) of system 10, in other examples, other modules of system 10 can perform any part of the technique shown in FIG. 8. As shown in FIG. 8, therapy module 18 may receive patient condition data from patient module 14 (126). The condition data may be, for example, physiological parameters sensed by sensor 22, from which patient conditions can be detected. Therapy module 18 may receive condition data at predetermined times according to a schedule, upon certain detected conditions of patient 12, or when requested by clinician module 16 or therapy module 18. In one example, therapy module 18 may receive the condition data once per day so that patient 12 is presented with a therapy regimen each day.

Upon receiving the condition data from patient module 14, therapy module 18 determines the patient condition indicated by the physiological parameter, thereby detecting the patient condition (128). In some examples, therapy module 18 may use the therapy instructions to detect the condition from the physiological parameters. In some examples, however, therapy module 18 may not determine the patient condition, but, instead, patient module 14 or clinician module 16 may determine the patient condition and transmit an indication of the patient condition detected based on the sensed physiological parameters to therapy module 18 via network 20.

Therapy module 18 automatically selects the therapy regimen associated with the detected condition (130). As described herein, the therapy regimen may be a contingent medication prescription that is transmitted to patient 12 upon detecting the condition associated with the therapy regimen stored in the therapy instructions.

Upon selecting the therapy regimen, therapy module 18 transmits the selected therapy regimen to patient module 14, which may present the therapy regimen to patient 12 (132). In some examples, the therapy regimen may include instructions for patient 12 to activate, deactivate, or modify a treatment that is used to manage the medical condition of patient 12. In these examples, patient module 14 may display the therapy regimen for review by patient 12 via patient interface 24. In other examples, the selected therapy regimen may include instructions to control a component of patient module 14 to automatically activate, deactivate, or modify a therapy automatically delivered to patient 12, e.g., an electrical stimulation therapy or a drug titration. In still other examples, the therapy regimen may be electronically delivered to a pill dispenser that dispenses the appropriate medication dose at the appropriate time. In this example, patient 12 may still be presented with the therapy regimen before dispensing. Other types of therapy regimens are contemplated.

Figure 9:
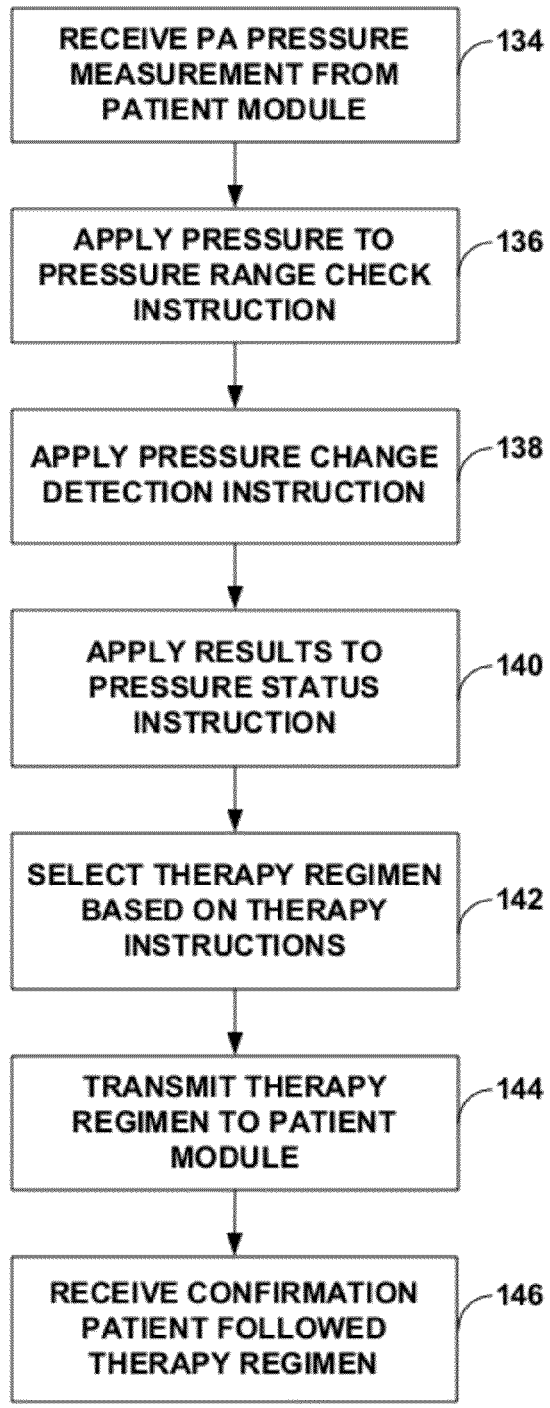
FIG. 9 is a flow diagram illustrating an example technique for selecting and transmitting a therapy regimen to a patient, where the therapy regimen is configured to treat congestive heart failure.

FIG. 9 is a flow diagram of an example technique that may be performed by therapy module 36 (FIG. 2) to select and transmit a therapy regimen to patient module 32 for treating congestive heart failure of patient 12. In examples in which patient 12 suffers from congestive heart failure, the instructions stored within therapy module 36 may receive, as input, a physiological parameter from sensor 40. This physiological parameter may be an indication of right ventricular pressure and/or pulmonary artery pressure of patient 12, and therapy module 36 may generate, as an output, a detected condition of patient 12 and an associated therapy regimen. The therapy instructions associating patient conditions with therapy regimens may be stored within the therapy instructions defined by clinician 15. In the example technique of FIG. 9, patient 12 may require daily monitoring to manage congestive heart failure. Thus, the technique shown in FIG. 9 may be performed daily, although other frequencies are contemplated, such as more than once daily or less often than one time per day. However, in some examples, the physiological parameters may be monitored more frequently (e.g., twice per day or three times per day) or less frequently (e.g., once per week or once per month) in other examples.

In the example technique shown in FIG. 9, therapy module 36 receives a daily pressure measurement from sensor 28 of patient module 32 (134). In some examples, the pressure measurement may be an individual ePAD pressure measurement collected at a particular time during the course of the day. In other examples, the pressure measurement may be an average, peak, or lowest ePAD pressure measurement, e.g., an average, peak or lowest ePAD pressure measurement, respectively, of a plurality of ePAD pressure measurements collected throughout the day. Therapy module 36 may use the daily pressure measurement as input for one or more condition instructions stored in therapy module 36. For example, in the example illustrated in FIG. 9, therapy module 36 determines a patient condition based on the received pressure measurement and parameters indicated by pressure range check (PRC) instruction module 58 (136). For example, therapy module 36 may determine the detected condition based on the daily pressure measurement and the stored ranges of PRC associated with respective conditions by PRC instruction module 58.

In addition, in the example illustrated in FIG. 9, therapy module 36 applies the received pressure to the pressure change detection (PCD) instruction module 60 (138). PCD module 60 determines whether the pressure measurements of patient 12 have changed significantly over a period of time based on the pressure change values indicated by PCD module 60. The period of time may be on the order of hours, days, weeks, or even months. The magnitude of change required over this time to indicate a significant change in pressure measurements is also defined by PCD module 60. Therapy module 36 may determine a patient condition based on the pressure range indicated by PRC module 58 and the pressure change indicated by PCD module 60. In some examples, PCD instruction module 60 may be used to detect a condition different than the condition detected by PRC instruction module 58. If PRC instruction module 58 detects a normal pressure condition, but PCD instruction module 60 detects that the pressure is increasing over time, though remaining in the normal (or "nominal") range, therapy module 18 may select a therapy regimen based on the changing pressure.

In other examples, the technique of FIG. 9 may only use one of PRC module 58 or PCD module 60 to detect the condition from the sensed physiological parameters. For example, the therapy instructions may indicate that for a specific physiological parameter, only the PRC module 58 may be used to select a therapy regimen based on the pressure range. In other examples, the therapy instructions may indicate that only the PCD module 60 may be used to detect the magnitude of change in the physiological parameters. In some examples, the therapy instructions may select one of PRC module 58 or PCD module 60 to detect the condition based on other patient information, e.g., electrical stimulation delivery, heart rate, or any other patient data.

Therapy module 36 uses the detected condition to automatically select a therapy regimen from the therapy instructions (142). The therapy regimen may be selected from a look-up table or using an equation or formula based upon the detected condition. As described in FIG. 1, the prescription may be a function of the detection condition instead of several independent prescriptions. Once the therapy regimen has been selected, therapy module 36 may transmit the therapy regimen to patient module 32 for presentation to patient 12 (144). In some examples, after patient 12 implements the therapy regimen, e.g., by taking the prescribed medication at the prescribed dosage, patient 12 may provide feedback indicating that the regimen was implemented, e.g., patient 12 took the medication. Therapy module 36 may then receive confirmation that patient 12 followed the therapy regimen from patient module 12 (146). In some examples, the confirmation may include answers to a questionnaire presented to patient 12.

Figure 10:
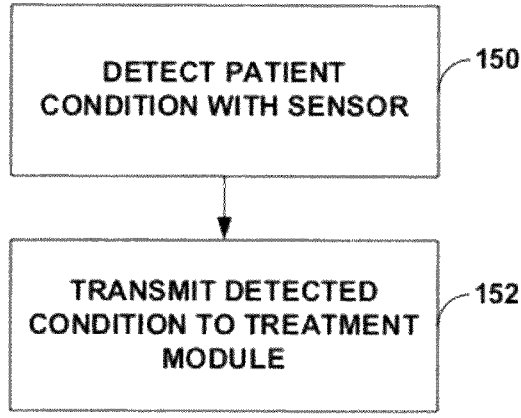
FIG. 10 is a flow diagram illustrating an example technique for detecting and transmitting a detected condition to the therapy module.

FIG. 10 is a flow diagram of an example technique that can be performed by patient module 14 (FIG. 1) to transmit patient condition data to therapy module 18. Therapy module 18 may utilize condition data from patient module 14, e.g., to detect a patient condition and select a therapy regimen. Condition data may include physiological parameters sensed by sensor 22, a raw output from sensor 22, or even a detected patient condition. In the example technique of FIG. 10, sensor 22 senses a physiological parameter of patient 12 (150). In some examples, patient module 14 may sense multiple types of physiological parameters with one sensor or patient module 14 may obtain physiological parameters from multiple different sensors. Once the condition is detected, patient module 14 transmits the detected condition to therapy module 18 (152). Therapy module 18 may then utilize the detected condition data to automatically select a therapy regimen from the therapy instructions previously defined by clinician 15.

Figure 11:
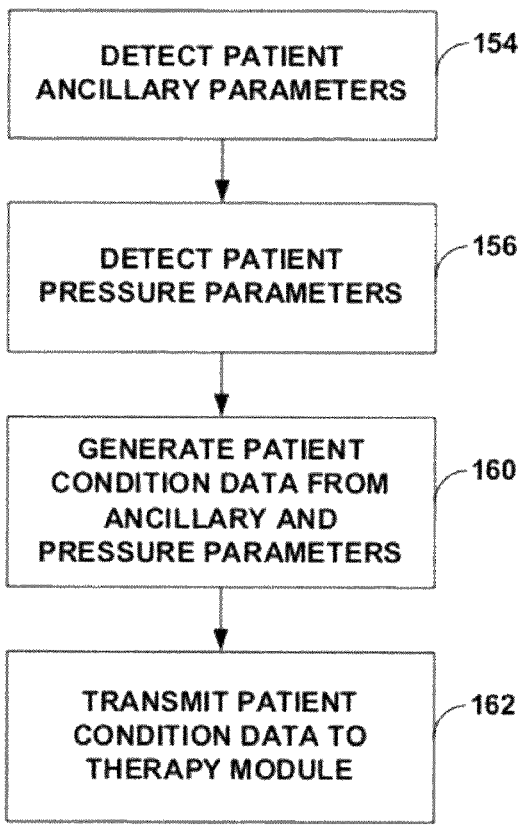
FIG. 11 is a flow diagram illustrating an example technique performed by the patient module illustrated in FIG. 2 for generating and transmitting patient conditions detected from ancillary and pulmonary artery pressures.

FIG. 11 is a flow diagram of an example technique that may be performed by patient module 32 (FIG. 2) to transmit patient condition data to therapy module 36. In the example technique illustrated in FIG. 11, one or more components of patient module 32 sense ancillary parameters of patient 12 (154). As described above, ancillary parameters may include any patient parameters that provide information indicative of the general health of patient 12. For example, ancillary parameters of patient 12 may include vital signs of patient 12, such as body temperature, blood pressure, pulse rate, and respiratory rate.

Patient module 32 may also sense physiological parameters, e.g., pulmonary pressures, for patient 12. One or more components of patient module 32 may sense daily patient pressure parameters used for detecting the condition of patient 12 (156). In some examples, sensor 40 may sense the daily patient pressure parameters by sensing right ventricular pressure of patient 12 used to derive the daily ePAD pressure of patient 12.

Patient module may generate patient condition data from the ancillary and pressure parameters (160). The generated patient condition data may include both the pressure data sensed by sensor 22 and other health related data. In some examples, the patient condition data may include an already detected condition after incorporating the ancillary data and sensed physiological parameters into the condition of patient 12. Patient module 32 may then transmit the combined patient conditions to therapy module 36 (162). Therapy module 36 may then utilize the condition data, e.g., both the ancillary parameters and the pressure data, to automatically select the associated therapy regimen according to the therapy instructions.

Figure 12:
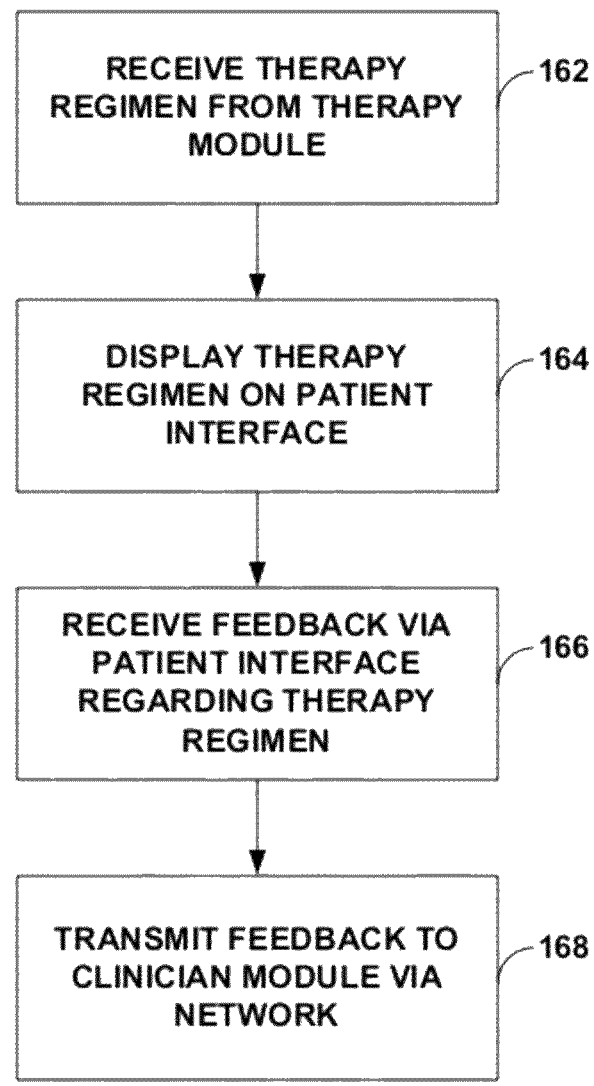
FIG. 12 is a flow diagram illustrating an example technique for displaying a therapy regimen to a patient and receiving feedback regarding the therapy regimen.

FIG. 12 is a flow diagram of a technique that may be performed by patient module 14 (FIG. 1) to display a therapy regimen selected based on a detected patient condition and receive feedback related to the displayed therapy regimen. In some examples, patient module 14 displays the therapy regimen via patient interface 24 for review by patient 12. In the example illustrated in FIG. 12, patient module 14 receives the automatically selected therapy regimen from therapy module 16 (162).

Patient module 14 may then display the therapy regimen to patient 12 via patient interface 24 (164). As described herein, the therapy regimen may be a contingent medication prescription. Patient 12 may modify an already used medication or take a new medication according to the therapy regimen. Additionally or alternatively, patient 12 may use the instructions from the therapy regimen to modify settings on a medical device used to treat the condition. In other examples, the therapy regimen may include software that is automatically uploaded to an implantable medical device or external medical device that delivers a drug therapy and/or an electrical stimulation therapy.

After the therapy regimen is presented to patient 12, patient module 14 may prompt patient 12 to provide feedback regarding the therapy regimen. This prompt may be generated after providing patient 12 with enough time to implement the therapy regimen (e.g., enough time to take the prescribed medication and for the medication to take effect). Patient interface 24 then receives the feedback from patient 12 regarding the therapy regimen (166). For example, the feedback may be related to one or more effects of the medication specified by the therapy regimen, e.g., side effects related to the treatment, effectiveness of the treatment, and the like. In other examples, the feedback may indicate to clinician 15 that patient 12 has followed the therapy regimen, e.g., has abided by the medication, dosage, timing instructions contained in the instruction set.

Upon receiving feedback from patient 12, patient module 14 may transmit the feedback to clinician module 16 (168) via network 20 for review by clinician 15. In some examples, clinician 15 may modify therapy regimens of the therapy instructions or one or more parameters of the condition identifiers or other methods used to detect the conditions of patient 12 based on the patient feedback.

Figure 13:
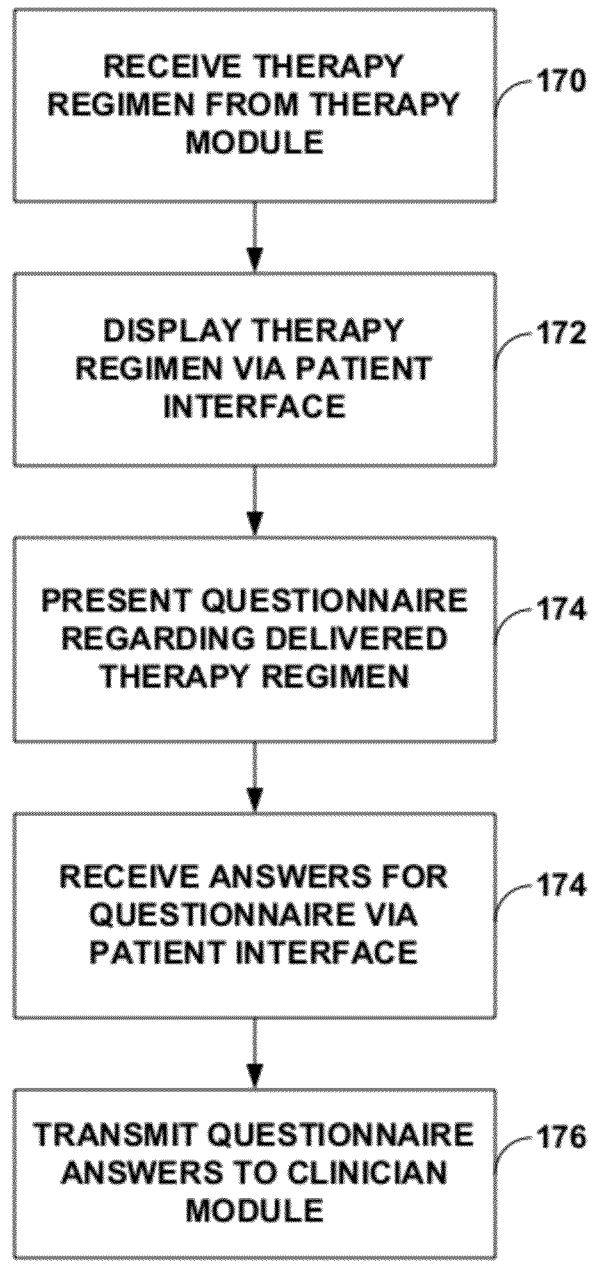
FIG. 13 is a flow diagram illustrating an example technique for displaying a selected therapy regimen to a patient and receiving questionnaire answers from the patient.

FIG. 13 is a flow diagram of an example technique that may be performed by patient module 32 (FIG. 2) to display a therapy regimen to treat congestive heart failure of patient 12 and receive feedback from patient 12 related to the therapy regimen. The technique of FIG. 13 may be similar to that of FIG. 12, but patient module 32 may also provide a questionnaire to patient 12 via patient interface 42 for review by patient 12. Questionnaires may also be used to manage patient conditions for other types of therapy.

Patient module 32 receives a therapy regimen from therapy module 46 (170) and displays the therapy regimen via patient interface 42 (172). The therapy regimen may be a set of instructions automatically selected by therapy module 46 based on the detected condition from one or more physiological parameters sensed by sensor 40. After patient 12 implements the therapy regimen, patient module 32 may also select a questionnaire regarding the therapy regimen and display the questionnaire on patient interface 42 for review by patient 12 (174). Patient 12 may then review the questionnaire and interact patient interface 42 to provide responses to the questions of the questionnaire. In this way, patient module 32 may receive answers for the questionnaire via patient interface 42 (174). Upon receiving the answers, patient module 32 may transmit the answers to clinician module 34 via network 15, e.g., for review by clinician 15 (176).

In some examples, therapy module 46 may automatically review the answers to the questionnaire. Therapy module 46 may then make automatic adjustments to the therapy instructions based upon the results of the questionnaire. For example, therapy module 46 may determine that a medication is not effective because the dose is too high. Therapy module 46 may then reduce the amount of medication to better respond to the complaints from patient 12 in the questionnaire. Clinician 15 may program therapy module 46 so that a certain range of changes to the dosage of medication or other adjustments to therapy are permitted. By limiting the extent to which therapy can be automatically adjusted by therapy module 46 based on the patient's answers to the questionnaire, clinician 15 may maintain some control over extensive changes to the therapy.

FIGS. 14A-14E illustrate example therapy regimens 178, 180, 182, 184, and 186 that may be displayed by patient interface 42 of patient module 32 (FIG. 2). In the examples illustrated in FIGS. 14A-14E, each of therapy regimens 178-186 correspond to a different condition, e.g., pressure state, of patient 12 as determined by the therapy instructions stored in therapy module 36. As described above, clinician module 34 may receive input from clinician 15 establishing therapy regimens associated with one or more conditions of a plurality of patient conditions in the form of the therapy instructions. In this manner, clinician 15 may define the detected conditions, therapy regimen, or even condition identifiers, such as the PRC and PCD values, which may be used to detect conditions from a sensed physiological parameter. Therapy module 36 may subsequently use the therapy instructions, along with physiological parameters of patient 12 received from patient module 32 and condition identifiers to detect conditions, e.g., pressure states, of patient 12. Therapy module 36 may then automatically select a therapy regimen associated with the detected condition by a therapy instruction, where the therapy regimen is selected to provide efficacious therapy to treat the congestive heart failure of patient 12.

FIG. 14A illustrates an example therapy regimen 178 that may be displayed to patient 12 via patient interface 42. Therapy regimen 178 may be automatically selected when therapy module 36 determines that the condition of patient 12 is normal, e.g., within an acceptable, satisfactory, or average pressure range. In the example of FIG. 14A, therapy regimen 178 instructs patient Jane Doe to maintain the same prescription that was instructed the day before and clearly describes the treatment regimen, e.g., describes the medication and dosage that patient Jane Doe should take. Therapy regimen 178 also includes the phrase "Transmitted today, check instructions again tomorrow" to indicate to patient 12 that the displayed therapy regimen is to be used for the date provided and patient 12 should check the therapy regimen transmitted tomorrow. This instruction may remind patient 12 to continue checking for new therapy regimens each day. This instruction is also provided in therapy regimens 180 and 184. In the examples of therapy regimens 182 and 186, patient 12 is instructed to call their clinic. In some examples, calling the clinic may be as simple as selecting the number presented on patient interface 24 and patient 14 may automatically connect patient 12 with the clinic.

FIGS. 14B and 14C illustrate example therapy regimens 180 and 182, respectively, which may be displayed to patient 12 via patient interface 42 when therapy module 36 detects the condition as a pressure state that is low and very low, respectively. In these examples, a low or very low pressure state may indicate that the physiological parameter sensed by sensor 22 is lower than an acceptable or normal threshold value or range of values. As illustrated, patient therapy regimens 180 and 182 each present new prescriptions for patient 12 (Jane Doe), e.g., instructions that are different than previous instructions presented to patient 12. In the examples illustrated in FIGS. 14B and 14C, patient instruction sets 180 and 182 include a "NEW PRESCRIPTION" indicator that may alert patient 12 to the fact that the therapy regimen includes instructions different than previously presented instructions.

In addition, therapy regimen 182, which corresponds to a very low pressure state of patient 12, displays instructions indicating that patient 12 should call a clinic because the very low pressure status of patient 12 may indicate a serious or severe progression of the congestive heart failure condition of patient 12. When the condition is severe, the contingent medication prescription may not be sufficient treatment alone. In these cases, more attentive care may be appropriate. In some cases, patient module 32, upon receiving the therapy regimen shown in FIG. 14C, may generate a notification that is transmitted to clinician module 34 via network 38, where the notification indicates the very low pressure state was detected and patient 12 may need attention.

FIGS. 14D and 14E illustrate example therapy regimens 184 and 186, respectively, which correspond to the conditions of a high pressure state and a very high pressure state, respectively, of patient 12. A high pressure state and a very high pressure state may indicate that that the physiological parameter sensed by sensor 22, e.g., the pulmonary pressure, is higher than an acceptable or normal threshold value or range of values. Therapy regimens 184 and each present new prescriptions for patient 12 (Jane Doe), e.g., instructions that are different than previous instructions presented to patient 12, and, therefore, include a "NEW PRESCRIPTION" indicator. In addition, therapy regimen 186, which corresponds to a very high pressure state of patient 12, displays instructions indicating that patient 12 should call a clinic because the very high pressure state of patient 12 may indicate a serious or severe progression of the congestive heart failure condition of patient 12. In some cases, patient module 32, upon receiving the therapy regimen shown in FIG. 14C, may generate a notification that is transmitted to clinician module 34 via network 38, where the notification indicates the very high pressure state was detected and patient 12 may need attention.

The example therapy regimens of FIGS. 14A-14E are merely examples. The contingent medication prescriptions may be presented in other forms.

In examples where patient module 14 includes a delivery device such as a pill dispenser, therapy regimens 178-186 may still be presented to patient 12. However, each therapy regimen may also include a set of instructions that are distributed directly to the pill dispenser and implemented by the pill dispenser. Then, the pill dispenser may only dispense the appropriate medication as directed by the therapy regimen. The pill dispenser may be useful to control dosages of more dangerous medications or for those patients in poor health and need extra assistance to use the appropriate medications and dosages.

FIGS. 15-19 illustrate example screens of a user interface implemented via a clinician module of an integrated patient care system, e.g., clinician module 16 of system 10 (FIG. 1) or clinician module 34 of system 30 (FIG. 2). These screens are only examples meant to provide an example of a user interface that presents information to clinicians. In some examples, the user interfaces shown in FIGS. 15-19 may be web pages. Therefore, clinician 15 may be able to access the screens of FIGS. 15-19 via any internet or intranet enabled computing device.

Figure 15:
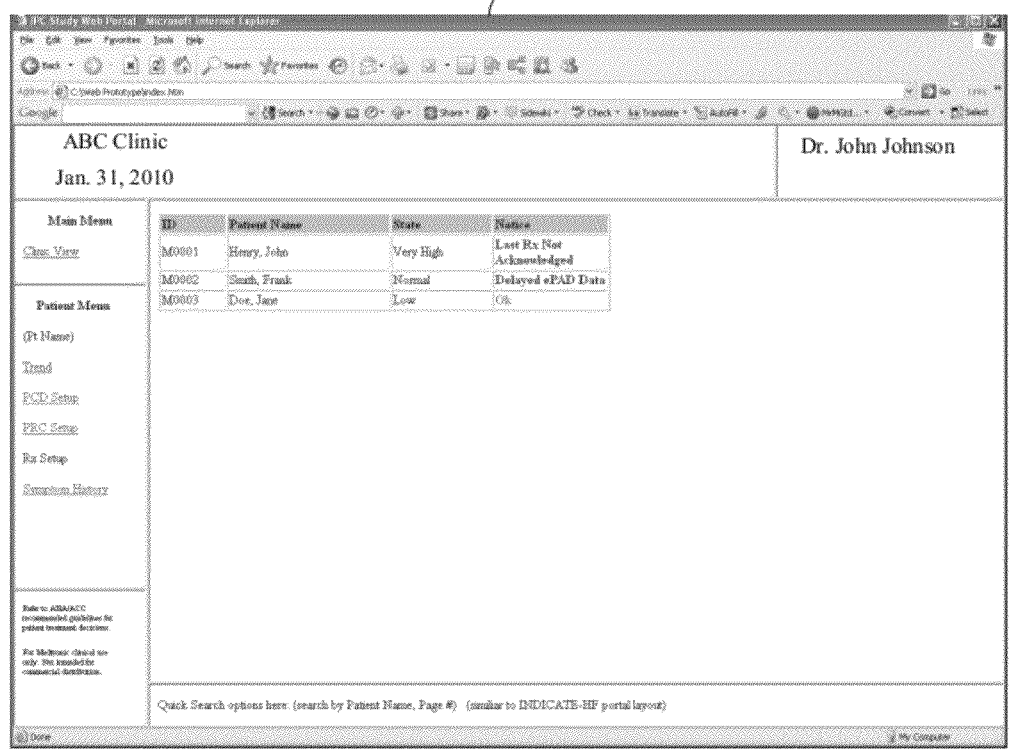
FIG. 15 is an example display that illustrates information related to the condition of several patients cared for by a single clinic.

FIG. 15 illustrates screen 188 which generally includes a visual summary of multiple patients in a clinic for review by clinician 15. Clinician 15 may view screen 188 to monitor the status of one or more patients under the clinician's care. Screen 188 may include the patient name, the patient identification number, the last detected condition, and any notices important to clinician 15 (e.g., notifications relating to certain detected patient conditions, such as relatively low pressure state). As shown in FIG. 15, screen 188 shows three patients that are being monitored for heart failure. The presented list of patients is sorted according to the detected condition, or pressure state, last received from the sensor. Screen 188 may also include a "Notice" section that provides information regarding the operational status of system 10, e.g., communication between each module or the function of a delivery device, or the latest feedback from patient 12. When more than one condition types are being monitored, each of the conditions may be presented in screen 188. In another field of screen 188, clinician 15 may be able to navigate to view historical condition data or even define the therapy instructions. In some examples, a therapy module of the integrated patient care system may transmit the information displayed via display 188 to the clinician module 16.

Figure 16:
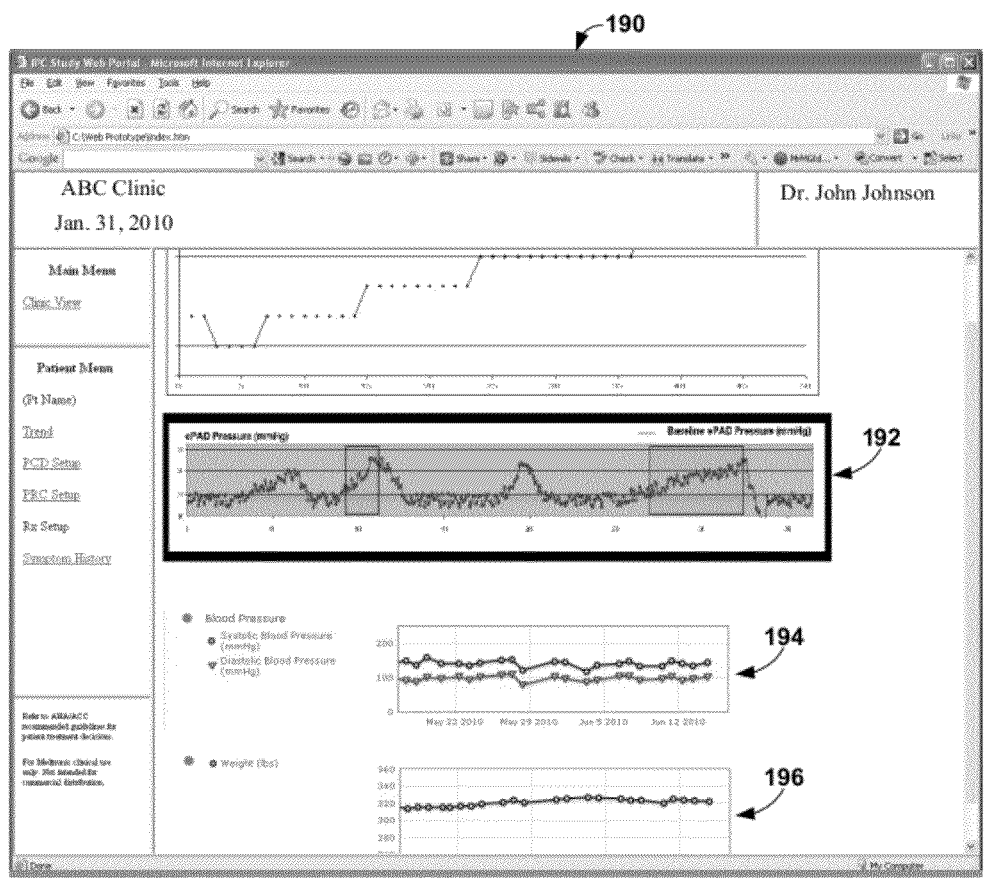
FIG. 16 is an example display that illustrates information related to condition data from one patient.

FIG. 16 illustrates screen 190 which may generally include graphs illustrating detected conditions of patient 12 over time. As shown in FIG. 16, screen 190 presents ePAD pressure graph 192, systemic blood pressure graph 194, and weight graph 196. Graph 192 provides detected condition data, e.g., the ePAD pressures, recorded over the last 30 days. As shown in graph 192, patient 12 was suffering from periodic increases in ePAD pressures. The portions of the pressure curves with high pressures are highlighted (e.g., outlined as shown in FIG. 16) for the convenience of clinician 15. Graph 192 also includes a baseline of normal ePAD pressures for patient 12, which graph 192 indicates was exceeded much of the time. Therefore, graph 192 may indicate that that the currently stored therapy regimens may not be effective in controlling the heart failure symptoms of patient 12.

Graphs 194 and 196 provide ancillary data regarding patient 12. Graph 194 provides trends of systemic diastolic and systolic blood pressures. Higher blood pressures may indicate a greater stress on the heart of patient 12, but lowering pressures may actually indicate an inability of the heart to maintain systemic blood pressure. Graph 196 provides the trend of patient1 12 weight. Because decompensation may be indicated by sudden changes in weight gain due to fluid retention, clinician 15 may desire to view weight changes over time.

FIG. 17 illustrates screen 198 which is an interactive user interface that displays historical condition data and receives input from a clinician for modifying the parameters of a pressure change detection (PCD) instruction 60. As described herein, the PCD instruction 60 is a condition identifier because it is one method to detect a condition from the physiological parameters sensed by a sensor of patient 12, e.g., sensor 22 or sensor 40. As shown in the example of FIG. 17, screen 198 includes graphs 200 and 202.

Graph 200 provides historical condition data in the form of ePAD pressures over the last 30 days. Graph 200 shows the change in ePAD pressures over the last 30 days. The change in pressures may be a change over a previous rolling average of pressures or a change with respect to the baseline pressures. In addition, graph 200 provides the graphical PCD instruction 60. The PCD instruction 60 may include PCD threshold 203 that is used to indicate when a high change condition has been reached. The therapy instructions defined by clinician 15 may include a therapy regimen associated when this condition is detected from the physiological parameters.

Threshold change buttons 204 may allow clinician 15 to adjust the value of the PCD threshold 203. Clinician 15 may save the new threshold 203 by selecting save button 206. However, clinician 15 may restore threshold 203 to the previous threshold by pressing restore button 208. In addition, clinician 15 may set threshold 210 to a nominal value when desired. In this manner, screen 198 may be used by clinician 15 to set the conditional identifier of PCD instruction module 60.

Figure 18:
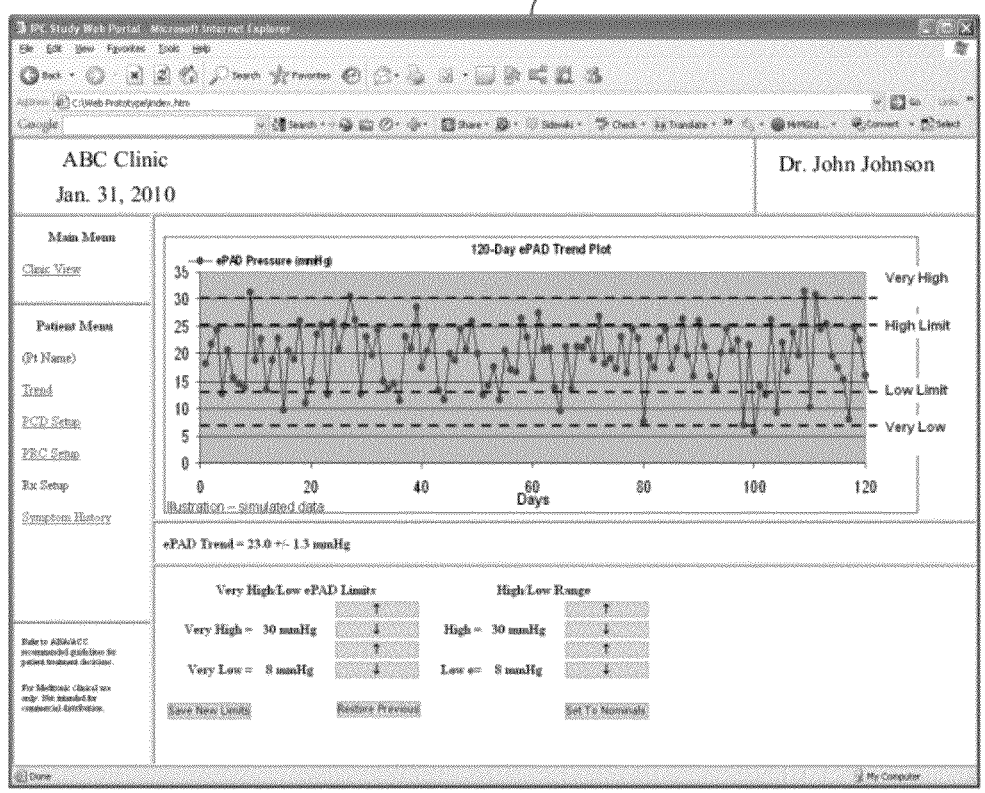
FIG. 18 is an example display that illustrates information related to detecting a patient condition based on a pressure range check.

FIG. 18 illustrates screen 212 which is an interactive user interface that can receive input from a clinician establishing one or more parameters that define the conditional identifiers of PRC instruction module 58. Screen 212 is substantially similar to screen 89 of FIG. 6. However, screen 212 is a web-based implementation of the PRC instruction 58. Therefore, clinician 15 may use screen 212 to overlay the therapy instructions on historical condition data to define and/or update a portion of the therapy instructions.

Figure 19:
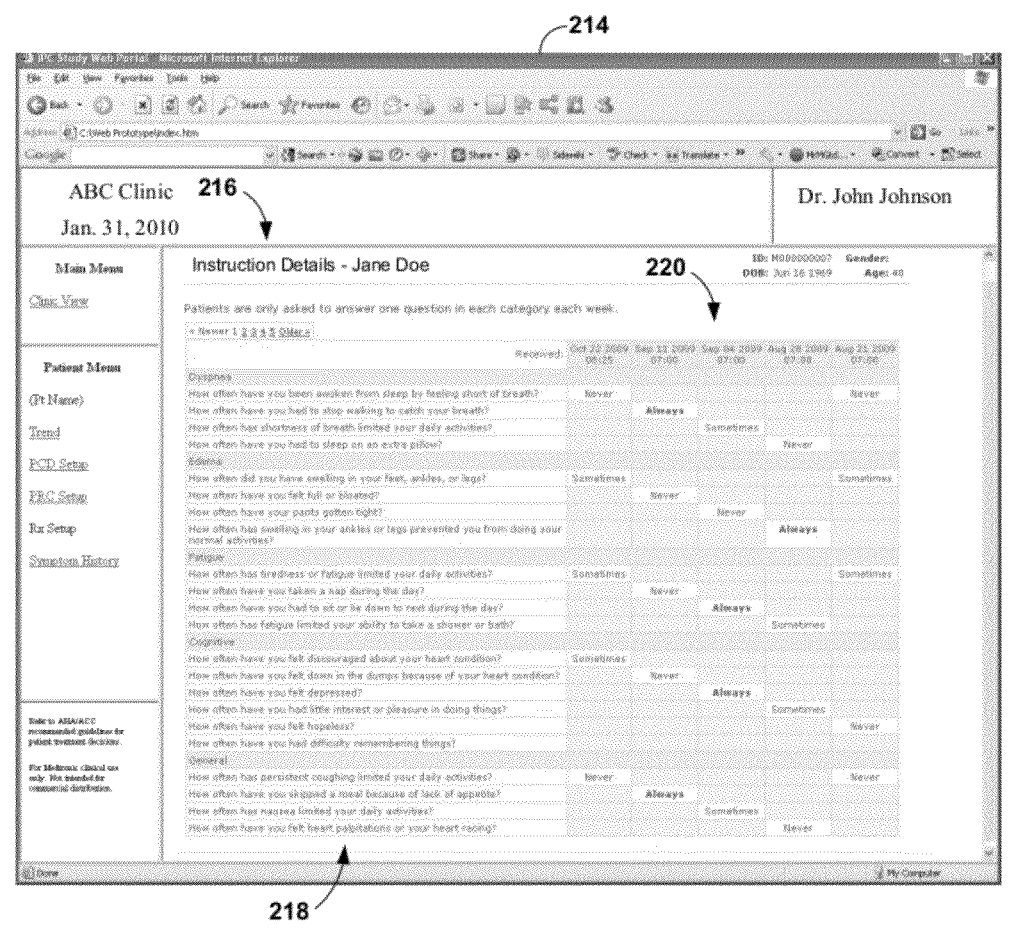

FIG. 19 illustrates screen 214 that is configured to receive patient feedback received from patient 12 regarding one or more therapy regimens or situations surrounding symptoms and therapy of patient 12. In the example illustrated in FIG. 19, patient module 32 receives input from patient 12 answering one or more questions of a questionnaire 216. Questionnaire 216 includes questions 218 that may be related to symptoms of the medical condition of patient (e.g., congestive heart failure), efficacy of the presented therapy regimens, or any other information related to patient 12. Questions 218 can be presented to patient 12 via patient interface 42, for example. Patient interface 42 received answers 220 to questions 218 from patient 12. Patient module 32 may transmit the completed questionnaire to clinician module 34 as feedback regarding the therapy.

Clinician 15 may use answers 220 to questionnaire 216 as an additional form of information to update the therapy instructions, including new contingent medication prescriptions. Although questionnaire 216 may provide feedback in response to every presented therapy regimen, patient 12 may not always be asked to do so. For example, patient 12 may be requested to provide feedback in the form of questionnaire only when the therapy regimen changes, when other detected conditions change substantially, or periodically (e.g., once a week). When patient 12 does not provide answers to a questionnaire, patient 12 may still provide feedback via patient module 32 that the therapy regimen was implemented.

Figure 21:
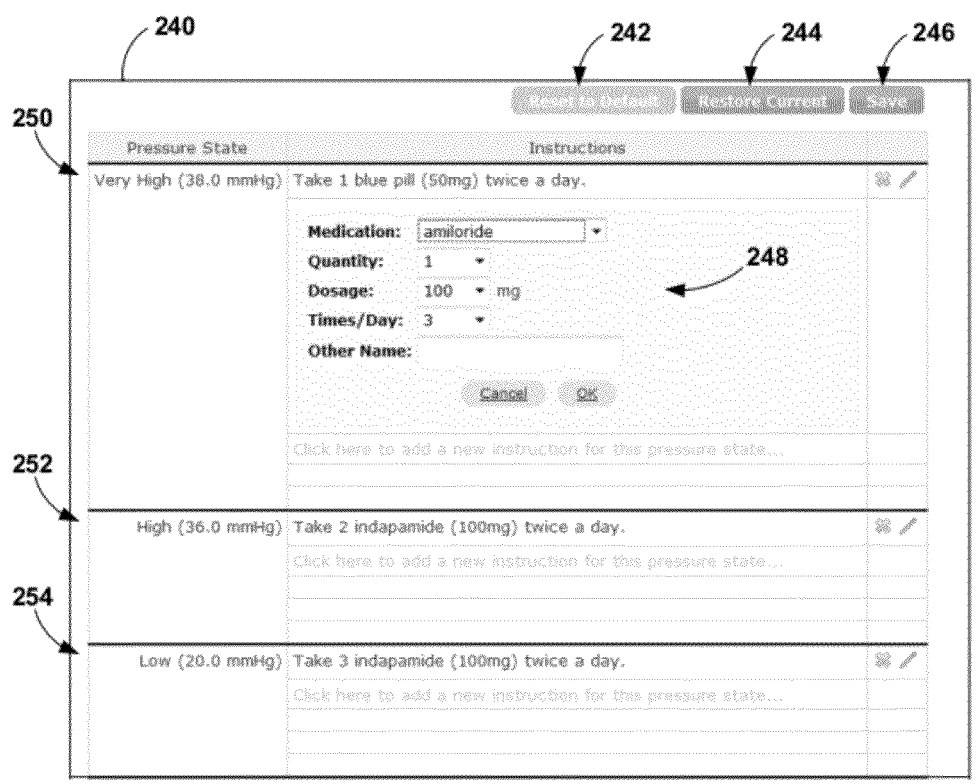

FIGS. 20 and 21 are conceptual diagrams illustrating example screens that may present and receive therapy instructions specifying contingent prescriptions from a clinician. Screens 230 and 240 shown in FIGS. 20 and 21, respectively, may be presented by clinician interface 26 of clinician module 16 in some examples. As shown in FIG. 20, screen 230 presents therapy regimens 234 for each of the conditions, which are displayed as pressure states 232. Some therapy regimens 234 include multiple prescriptions and/or an instruction to call the clinic. For example, the therapy regimen for the very high pressure state includes taking Drugs A and B while also calling the clinic. In another example, the therapy regimen for the very low pressure state is no medication and instructions (e.g., textual, audio, and/or somatosensory) to a call to the clinic.

When clinician 15 modifies therapy regimens 234 by interacting with screen 230, clinician 15 selects the delete input 236 or edit input 238 that corresponds to the specific therapy regimen that is to be deleted or changed. For example, selecting delete input 236 for the high pressure state would remove the therapy regimen that indicates patient 12 should take 3 Drug A pills from the high pressure state condition. Similarly, clinician 15 may select edit input 238 and screen 230 may allow clinician 15 to modify the instructions corresponding to therapy regimens 234, e.g., by directly editing the text displayed in the proper instruction text box 234. In another example, selecting edit input 238 may prompt user interface 26 to present screen 240 of FIG. 21.

Screen 240 can be presented by clinician interface 26 and allows clinician 15 to set the therapy regimen for a particular condition. In the example shown in FIG. 21, regimen input 248 includes pull down menus for entering details about the therapy regimen, e.g., the type of medication, the quantity, the dosage, and the number of times each day. In some examples, clinician 15 may enter additional notes, such as notes about another name for the medication or other information for patient 12. In other examples regimen input 248 may provide other input mechanisms, such as text boxes that allow clinician 15 to directly enter text or numbers instead of using a pull down menu. Once the therapy regimen is set, clinician 15 may select the "OK" object to store the new prescription as the therapy regimen or select "cancel" to cancel the prescription.

In the example shown in FIG. 21, regimen input 248 is shown as being associated with the condition of very high pressure state 250. In other examples, similar screens may be displayed in which regimen input 248 is provided to set the therapy regimens of high pressure state 252, low pressure state 254, or other conditions now shown in FIG. 21. Screen 240 also includes default input 242, restore input 244, and save input 246. Default input 242 may reset all of the therapy regimens or just the currently displayed therapy regimen (associated with a particular patient input) to a patient condition. The default can be determined by clinician 15 in some examples, and may be specific to patient 12 or may be general to more than one patient with similar medical conditions. Restore input 244 may reset all of the therapy regimens to the previously stored state. Save input 246 may be selected to save the newly update therapy regimens as entered using regimen input 248. Screen 240 is just one example of a screen that accepts changes to the therapy regimens, but clinician interface 26 may allow clinician 15 to modify therapy regimens and set other therapy instructions using other input methods.

The techniques described herein allow for automated monitoring of a patient condition and automated delivery of a therapy regimen to the patient based upon the monitoring. In this manner, these techniques may allow for more frequent patient monitoring and/or specified therapy via contingent prescriptions for medication. Clinician 15 may preset each therapy regimen as a contingent prescription for the patient, and the system may automatically deliver one of the contingent prescriptions upon detection of a condition associated with the contingent prescriptions. This technique may reduce the time required by a clinician to monitor the patient and, at the same time, increase therapy responsiveness to the patient.

The techniques may utilize one or more sensors that detect conditions of the patient, e.g., ranges of physiological parameters, and transmit the detected condition to a treatment module. The treatment module may compare select one of the therapy regimens based on which therapy instructions are associated with the detected condition, as previously defined by a clinician. A clinician may update the associations, conditions, or even therapy instructions with the aid of historical condition data presented to clinician 15. These techniques for delivering contingent prescriptions may benefit those patients suffering from heart failure away from a health care facility. Updating medications quickly may provide improved therapy and quality of life for quickly changing symptoms associated with congestive heart failure.

The techniques described in this disclosure, including those attributed to patient module 14, clinician module 16, therapy module 18, patient module 32, clinician module 34, therapy module 36, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by a specific module 14, 16, 18, 32, 34, 36, any one or more parts of the techniques described herein may be implemented by a processor of one of the modules 14, 16, 18, 32, 34, 36, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure. Any computer-readable medium described herein may be an article of manufacture and may be nontransient.

Various examples have been described for treatment of a patient. These examples may include generating therapy instruction sets, sensing physiological parameters indicative of one or more conditions with a sensor, comparing the sensed parameters with the therapy instructions, and selecting a therapy regimen based upon the comparison. These techniques may be employed across various devices communicating via a network to monitor and treat the patient remotely. Any combination of clinician instructions, comparisons with physiological parameters, and selection of therapy regimens is contemplated. These and other examples are within the scope of the following claims.

The invention claimed is:

1. A system comprising:
   a pressure sensor configured to sense pulmonary artery pressure indicative of heart failure;
   a first instruction module to determine a first condition indication of the sensed pulmonary artery pressure;

a second instruction module to determine a second condition of the sensed pulmonary artery pressure, the first condition being a pressure range and the second condition being pressure change;

a clinician module configured to receive input that defines one or more therapy instructions specific to a patient and to determine whether to use one or both of the first condition and the second condition to select a therapy regimen from a plurality of stored therapy regimens; and a patient display configured to present the selected therapy regimen to the patient.

2. The system of claim 1, wherein the therapy instructions associate each therapy regimen of the plurality of stored therapy regimens with at least one of the conditions, and the processor is configured to select the therapy regimen from the plurality of stored therapy regimens based on detection of the associated condition.

3. The system of claim 2, wherein each therapy regimen of the plurality of stored therapy regimens comprise a contingent medication prescription that is only presented to the patient based on the one or more conditions.

4. The system of claim 1, further comprising:
a patient module comprising a patient telemetry module configured to receive the selected therapy regimen from the clinician module; and
a patient interface including the patient display and configured to receive input from the patient.

5. The system of claim 4, wherein the patient interface is configured to receive feedback from the patient related to the selected therapy regimen and a perceived condition of the patient, wherein the feedback comprises at least one answer to at least one question of a questionnaire presented by the patient interface, and the patient telemetry module is configured to transmit the feedback to the clinician module for presentation to the clinician.

6. The system of claim 1, wherein the one or more therapy instructions comprise a condition identifier, and wherein the condition identifier comprises at least one of a pressure range check instruction and a pressure change detection instruction, or a patient pressure status instruction.

7. The system of claim 1, wherein the first condition further comprises at least one of a normal pressure state, a low pressure state, a very low pressure state, a high pressure state, or a very high pressure state.

8. The system of claim 1, wherein the plurality of stored therapy regimens comprises at least one of a medication type, a medication dosage, and a delivery time.

9. The system of claim 1, further comprising a pill dispenser configured to receive the selected therapy regimen from the clinician module and dispense a medication according to the therapy regimen.

10. The system of claim 1, wherein the clinician module comprises a clinician interface, wherein the clinician module is configured to graphically present historical physiological parameter data of the patient via the clinician interface, graphically overlay parameters that define at least one of the first condition and the second condition over the historical physiological parameter data, and receive input from the clinician that updates the parameters that define the at least one of the first condition and the second condition based on the historical physiological parameter data.

11. The system of claim 1, further comprising a treatment module that comprises a memory, wherein the treatment module is configured to receive the one or more therapy instructions from the clinician module via a network, store the one or more therapy instructions in the memory, and receive the sensed pulmonary artery pressure from the sensor via the network.

12. A method comprising:
receiving input from a clinician at a clinician module, wherein the input defines one or more therapy instructions specific to a patient;
sensing pulmonary artery pressure indicative of heart failure with a pressure sensor;
determining a first condition indication of the sensed pulmonary artery pressure with a first instruction module;
determining a second condition indication of the sensed pulmonary artery pressure with a second instruction module, the first condition being a pressure range and the second condition being pressure change;
determining whether to use one or both of the first condition and the second condition to select a therapy regimen from a plurality of stored therapy regimens; and
presenting the selected therapy regimen to the patient via a patient display.

13. The method of claim 12, wherein the therapy instructions associate each therapy regimen of the plurality of stored therapy regimens with at least one of the conditions, and wherein selecting the therapy regimen comprises automatically selecting the at least one therapy regimen based on detection of the one or more associated conditions.

14. The method of claim 13, wherein each therapy regimen of the plurality of stored therapy regimens comprises a contingent medication prescription that is only presented to the patient upon detection of the associated condition.

15. The method of claim 13, further comprising:
receiving the selected therapy regimen with a patient telemetry module of a patient module; and
receiving input from the patient in response to the presented therapy regimen via a patient interface that includes the patient display.

16. The method of claim 15, further comprising:
receiving feedback from the patient via the patient interface related to the selected therapy regimen and a perceived condition of the patient, wherein the feedback comprises at least one answer to at least one question of a questionnaire presented by the patient interface; and
transmitting the feedback to the clinician module for presentation to the clinician via the patient telemetry module.

17. The method of claim 12, wherein the first condition further comprises at least one of a normal pressure state, a low pressure state, a very low pressure state, a high pressure state, or a very high pressure state.

18. The method of claim 12, wherein each of the plurality of stored therapy regimens comprises at least one of a medication type, a medication dosage, and a delivery time.

19. The method of claim 12, further comprising:
graphically presenting historical physiological parameter data via a clinician interface of the clinician module;
graphically overlaying parameters that define at least one of the first condition and the second condition over the historical physiological parameter data; and
receiving input from the clinician that updates the parameters that define the at least one of the first condition and the second condition based on the historical physiological parameter data.

20. The method of claim 12, further comprising:
receiving the one or more therapy instructions at a therapy module from the clinician module via a network;
storing the one or more therapy instructions in a memory of the therapy module; and receiving the physiological parameter from the sensor at the treatment module via the network.

21. A system comprising:

means for receiving input from a clinician that defines one or more therapy instructions specific to a patient;

means for sensing pulmonary artery pressure of the patient;

means for determining a first condition indication of the sensed pulmonary artery pressure;

means for determining a second condition of the sensed pulmonary artery pressure, the first condition being a pressure range and the second condition being pressure change;

means for determining whether to use one or both of the first condition and the second condition to select a therapy regimen from a plurality of stored therapy regimens; and means for presenting the selected therapy regimen to the patient.

* * * * *